US009572910B2

(12) United States Patent
Messersmith et al.

(10) Patent No.: US 9,572,910 B2
(45) Date of Patent: *Feb. 21, 2017

(54) PH RESPONSIVE SELF-HEALING HYDROGELS FORMED BY BORONATE-CATECHOL COMPLEXATION

(75) Inventors: Phillip B. Messersmith, Clarendon Hills, IL (US); Lihong He, Wilmette, IL (US); Dominic E. Fullenkamp, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/476,422

(22) Filed: May 21, 2012

(65) Prior Publication Data

US 2012/0329882 A1    Dec. 27, 2012

Related U.S. Application Data

(60) Provisional application No. 61/488,020, filed on May 19, 2011.

(51) Int. Cl.

| | | |
|---|---|---|
| *A61K 31/80* | (2006.01) | |
| *A61L 27/18* | (2006.01) | |
| *A61L 15/26* | (2006.01) | |
| *A61K 9/06* | (2006.01) | |
| *C08F 120/56* | (2006.01) | |
| *C08G 65/328* | (2006.01) | |
| *C08G 65/337* | (2006.01) | |
| *C08F 220/34* | (2006.01) | |

(52) U.S. Cl.
CPC .............. *A61L 27/18* (2013.01); *A61K 9/06* (2013.01); *A61L 15/26* (2013.01); *C08F 120/56* (2013.01); *C08F 220/34* (2013.01); *C08G 65/328* (2013.01); *C08G 65/337* (2013.01); *C08G 2650/50* (2013.01)

(58) Field of Classification Search
USPC ..................................................... 424/78.37
See application file for complete search history.

(56) References Cited

U.S. PATENT DOCUMENTS

| | | | |
|---|---|---|---|
| 2008/0247984 A1* | 10/2008 | Messersmith et al. .... | 424/78.02 |
| 2010/0099586 A1* | 4/2010 | De Benedictis et al. ..... | 507/219 |
| 2011/0052788 A1 | 3/2011 | Messersmith et al. | |

FOREIGN PATENT DOCUMENTS

| | | |
|---|---|---|
| EP | 1431300 A1 | 6/2004 |
| WO | 2004063388 A2 | 7/2004 |
| WO | 2009062146 A2 | 5/2009 |

OTHER PUBLICATIONS

Matsunaga, Structure and Characterization of Tetra-PEG gel by small-Angle Neutron Scattering, Macromolecules, vol. 42, No. 4, pp. 1344-1351, Feb. 3, 2009.*
Asher, et al., Photonic Crystal Carbohydrate Sensors: Low Ionic Strength Sugar Sensing, J. Am. Chem. Soc., 2003, 125:3322-3329.
Bilic, et al., Injectable Candidate Sealants for Fetal Membrane Repair: Bonding and Toxicity In Vitro, Am. J. Obstet. Gynecol., 2010, 202(1):85.e1-85.e9.
Brubaker, et al., Biological Performance of Mussel-Inspired Adhesive in Extrahepatic Islet Transplantation, Biomaterials, 2010, 31(3):420-427.
Chen, et al., Polyvinylamine-Phenylboronic Acid Adhesion to Cellulose Hydrogel, Langmuir, 2009, 25(12):6863-6868.
Deng, G., et al., Covalent Cross-Linked Polymer Gels with Reversible Sol-Gel Transition and Self-Healing Properties, Macromolecules, 2010, 43(3):1191-1194.
Deng, W., et al., A Chemical-Responsive Supramolecular Hydrogel from Modified Cyclodextrins, Angew. Chem. Int. Ed., 2007, 46(27):5144-5147.
Dowlut, et al., An Improved Class of Sugar-Binding Boronic Acids, Soluble and Capable of Complexing Glycosides in Neutral Water, J. Am. Chem. Soc., 2006, 128(13):4226-4227.
Drury, et al., Hydrogels for Tissue Engineering: Scaffold Design Variables and Applications, Biomaterials, 2003, 24:4337-4351.
Elisseeff, Hydrogels: Structure Starts to Gel, Nature Materials, 2008, 7:271-273.
Fang, et al., Progress in Boronic Acid-Based Fluorescent Glucose Sensors, Journal of Fluorescence, 2004, 14(5):481-489.
Gong, Why are Double Network Hydrogels So Tough?, Soft Matter, 2010, 6:2583-2590.
Iddon, et al., Synthesis of Stimulus-Responsive Block Copolymer Gelators by Atom Transfer Radical Polymerisation, European Polymer Journal, 2007, 43(4):1234-1244.
Lee, B., et al., Synthesis and Gelation of DOPA-Modified Poly(ethylene glycol) Hydrogels, Biomacromolecules, 2002, 3:1038-1047.
Lee, B., et al., Mussel-Inspired Adhesives and Coatings, Annu. Rev. Mater. Res., 2011, 41:99-132.
Lee, H., et al., Single-Molecule Mechanics of Mussel Adhesion, PNAS, 2006, 103(35):12999-13003.
Lee, H., et al., Mussel-Inspired Surface Chemistry for Multifunctional Coatings, Science, 2007, 318(5849):426-430.
Li, et al. Synthesis and Characterization of Biocompatible Thermo-Responsive Gelators Based on ABA Triblock Copolymers, Biomacromolecules, 2005, 6(2):994-999.
Mancilla, et al., Asymmetric Synthesis of New Bicyclic Phenylboronic Esters Containing Configurationally Stable Chiral Nitrogen and Boron, Journal of Organometallic Chemistry, 1987, 321:191-198.
Napolitano, et al., A New Oxidation Pathway of the Neurotoxin 6-aminodopamine. Isolation and Characterisation of a Dimer with a Tetrahydro[3,4a] Iminoethanophenoxazine Ring System, Tetrahedron, 1992, 48(39):8515-8522.

(Continued)

*Primary Examiner* — Adam C Milligan
(74) *Attorney, Agent, or Firm* — Quarles and Brady, LLP

(57) ABSTRACT

Biocompatible hydrogels made from cross-linked catechol-borate ester polymers are disclosed, along with methods of synthesizing and using such hydrogels. The hydrogels of the present invention are prepared by boronic acid-catechol complexation between catechol-containing macromonomers and boronic acid-containing cross-linkers. The resulting hydrogels are pH-responsive and self-healing, and can be used in a number of different biomedical applications, including in surgical implants, in surgical adhesives, and in drug delivery systems is data provides further evidence of the viability of using the disclosed hydrogels for in vivo in biomedical applications.

11 Claims, 32 Drawing Sheets

(56) References Cited

OTHER PUBLICATIONS

O'Lenick, et al., Thermosensitive Aqueous Gels with Tunable Sol-Gel Transition Temperatures from Thermo- and pH-Responsive Hydrophilic ABA Triblock Copolymer, Langmuir, 2010, 26(11):8787-8796.
Paugam, et al., Selective Dopamine Transport Using a Crown Boronic Acid, J. Am. Chem. Soc., 1994, 116:11203-11204.
Peppas, et al., Hydrogels in Pharmaceutical Formulations, European Journal of Pharmaceutics and Biopharmaceutics, 2000, 50:27-46.
Peppas, et al., Hydrogels in Biology and Medicine: From Molecular Principles to Bionanotechnology, Adv. Mater., 2006, 18:1345-1360.
Pizer, et al., Mechanism of the Complexation of Boron Acids with Catechol and Substituted Catechols, Inorg. Chem., 1977, 16(7):1677-1681.
Pizer, et al. Thermodynamics of Several 1:1 and 1:2 Complexation Reactions of the Borate Ion with Bidentate Ligands. 11B NMR Spectroscopic Studies, Inorg. Chem, 1994, 33(11):2402-2406.
Ren, et al., Dual-Responsive Supramolecular Hydrogels from Water-Soluble PEG-Grafted Copolymers and Cyclodextrin, Macromolecular Bioscience, 2009, 9(9):902-910.
Roberts, et al., Dynamically Restructuring Hydrogel Networks Formed with Reversible Covalent Crosslinks, Advanced Materials, 2007, 19(18):2503-2507.
Roberts, et al., Chemorheology of Phenylboronate-Salicylhydroxamate Cross-Linked Hydrogel Networks with a Sulfonated Polymer Backbone, Macromolecules, 2008, 41(22):8832-8840.
Sfika, et al., Association Phenomena of Poly(acrylic acid)-b-poly(2-vinylpyridine)-b-poly(acrylic acid) Triblock Polyampholyte in Aqueous Solutions: From Transient Network to Compact Micelles, Macromolecules, 2003, 36(13):4983-4988.
Shabbir, et al., Pattern-Based Recognition for the Rapid Determination of Identity, Concentration, and Enantiomeric Excess of Subtly Different Threo Diols, J. Am. Chem. Soc., 2009, 131(36):13125-13131.
Shen, et al., Dynamic Properties of Artificial Protein Hydrogels Assembled Through Aggregation of Leucine Zipper Peptide Domains, Macromolecules, 2007, 40(3):689-692.
Springsteen, et al., A Detailed Examination of Boronic Acid-Diol Complexation, Tetrahedron, 2002, 58:5291-5300.
Tomatsu, et al., Photoresponsive Hydrogel System Using Molecular Recognition of a-Cyclodextrin, Macromolecules, 2005, 38(12):5223-5227.
Tsitsilianis, Responsive Reversible Hydrogels from Associative "Smart" Macromolecules, Soft Matter, 2010, 6:2372-2388.
Winblade, et al., Sterically Blocking Adhesion of Cells to Biological Surfaces with a Surface-Active Copolymer Containing Poly(ethylene glycol) and Phenylboronic Acid, Journal of Biomedical Materials Research, 2002, 59(4):618-631.
Yan, et al., The Relationship Among pKa, pH, and Binding Constants in the Interactions Between Boronic Acids and Diols—It Is Not As Simple As It Appears, Tetrahedron, 2004, 60(49):11205-11209.
Guvendiren, et al., Self-Assembly and Adhesion of DOPA-Modified Methacrylic Triblock Hydrogels, Biomacromolecules, 2008, 9:122-128.
He, et al., pH Responsive Self-Healing Hydrogels Formed by Boronate-Catechol Complexation, Chem. Commun., 2011, 47:7497-7499.
Su, et al., Catechol Polymers for pH-Responsive, Targeted Drug Delivery to Cancer Cells, J. Am. Chem. Soc., 2011, 133:11850-11853.
PCT International Search Report and Written Opinion, PCT/US2012/038798, Jun. 28, 2013, 11 pages.

* cited by examiner

PH RESPONSIVE SELF-HEALING HYDROGELS FORMED BY BORONATE-CATECHOL COMPLEXATION

CROSS-REFERENCE TO RELATED APPLICATIONS

This application claims the benefit of U.S. Provisional Application No. 61/488,020, filed May 19, 2011, which is incorporated by reference herein in its entirety.

STATEMENT REGARDING FEDERALLY-SPONSORED RESEARCH OR DEVELOPMENT

This invention was made with government support under grant numbers RC1 DE020702 and R37 DE014193 awarded by the National Institutes of Health. The government has certain rights in the invention.

FIELD OF THE INVENTION

This disclosure is directed to hydrogels, specifically pH responsive self-healing hydrogels comprising covalently cross-linked polymers formed by boronic acid-catechol complexation, as well as to methods of synthesizing and using the hydrogels.

BACKGROUND OF THE INVENTION

The complexation of diols and boronic acid in aqueous solution results in reversible covalent bonding through the formation of a boronate ester linkage, and this reaction has been extensively used in biomedical application as an efficient method of detecting sugar under specific conditions (see Asher et al. *J. Am. Chem. Soc.* 2003, 125, 3322-3329; Dowlut, et al. *J. Am. Chem. Soc.* 2006, 128, 4226; Winblade et al. *J. Biomedical Materials Research* 2001, 59, 618). The complexation reaction occurs at solution pH which is higher than the pKa of the two reagents used (see Yan et al. *Tetrahedron* 2004, 60, 11205-11209; Springsteen et al. *Tetrahedron* 2002, 58, 5291). Because the pKa of phenyl boronic acid is very high (~8.8), this complexation reaction has not been generally reported to occur under physiological conditions.

Hydrogels are made from three-dimensional polymeric networks, which are hydrophilic and cross-linked via covalent or non-covalent interactions. Because they are homogenous soft materials with physical properties similar to those of soft tissues, there is great interest in using hydrogels for a number of biomedical applications, including in sensors, in separation systems, and in various biomaterials. Recently, efforts have focused on stimuli-responsive hydrogels, which have the ability to respond to external triggers like pH, temperature, and light. This ability to respond to conditions in the surrounding environment makes such hydrogels suitable for a range of applications in medicine and tissue engineering.

Research on stimuli-responsive hydrogels has specifically focused on physical (non-covalently bonded) hydrogels. However, physical hydrogels are generally less stable and have poorer mechanical properties than covalently cross-linked hydrogels. Therefore, there is a need in the art for hydrogels that integrate into a single material the stimuli-responsiveness of certain physical gels with the stability provided by chemical (covalently bonded) hydrogels. Ideally, such hydrogels would be self-healing and would form under physiological conditions.

BRIEF DESCRIPTION OF THE INVENTION

The present disclosure provides pH responsive, self-healing, biocompatible hydrogels comprising cross-linked polymers made using boronic acid-catechol complexation to form a boronate ester covalent bond. Accordingly, in a first aspect, the disclosure encompasses a hydrogel that includes a cross-linked polymer. The cross-linked polymer is made up of (a) a plurality of macromonomers comprising at least four terminal catechol moieties and having a molecular weight of 1,000 to 20,000 Daltons; and (b) one or more cross-linkers comprising two or more terminal boronic acid moieties. The catechol moieties of the macromonomers are covalently bonded to the boronic acid moieties of the cross-linkers to form a tetrahedral borate ester, whereby the macromonomers are cross-linked into a polymer. In some embodiments, the macromonomers have a molecular weight of 5,000 to 15,000 Daltons.

In certain embodiments, the macromonomers are polyethylene glycols or (dihydroxyphenyl)ethyl methacrylamide copolymers. In some such embodiments, the polyethylene glycols are 4-arm polyethylene glycols wherein each arm is terminated with a catechol moiety. Optionally, the 4-arm polyethylene glycols have the structure:

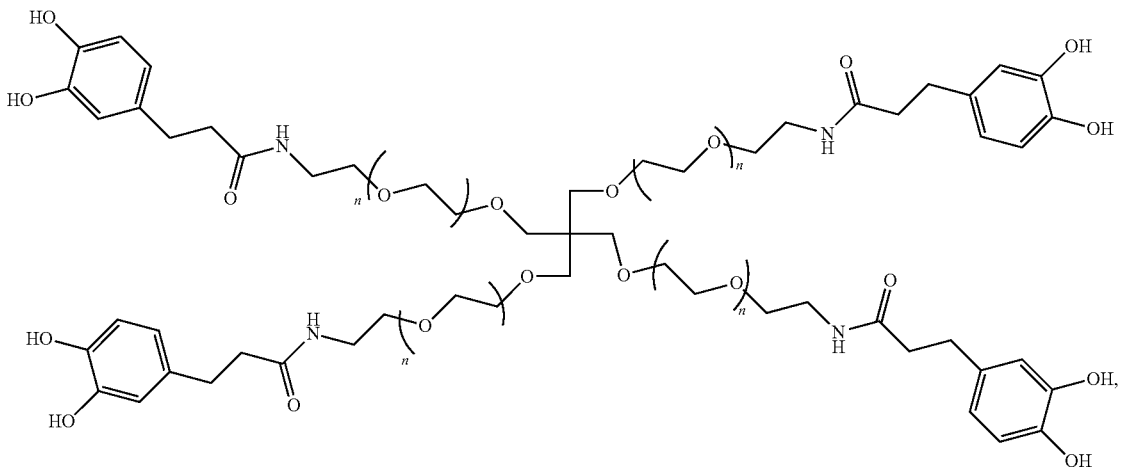

wherein each n is independently selected to be from 1 to 200.

In other such embodiments, the (dihydroxyphenyl)ethyl methacrylamide copolymers are comprised of (dihydroxyphenyl)ethyl methacrylamide monomers, wherein the phenyl group is nitro substituted. Optionally, the (dihydroxyphenyl)ethyl methacrylamide copolymers may have the structure:

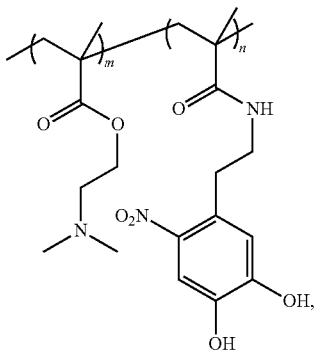

-continued

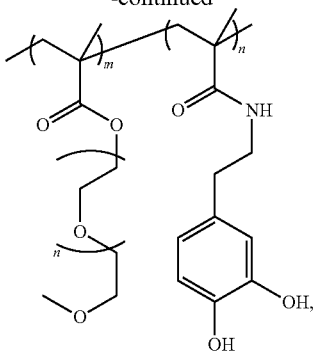

wherein each of m, n and a are independently selected to be from 1 to 200.

In certain embodiments, the two terminal boronic acid moieties on the cross-linkers are attached to an aromatic ring. In such embodiments, the two terminal boronic acid moieties on the cross linkers may be attached to the same aromatic ring or to two different aromatic rings on opposite ends of the cross-linkers.

In certain embodiments, the cross-linkers have the structure:

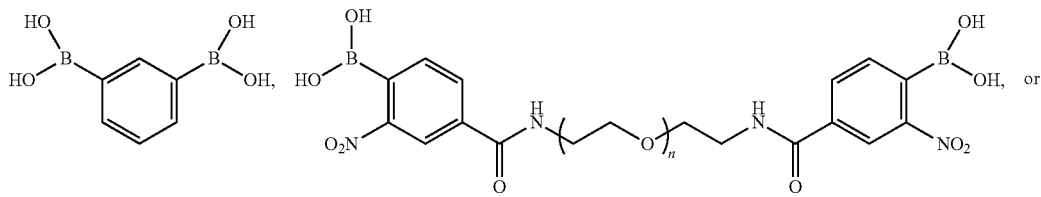

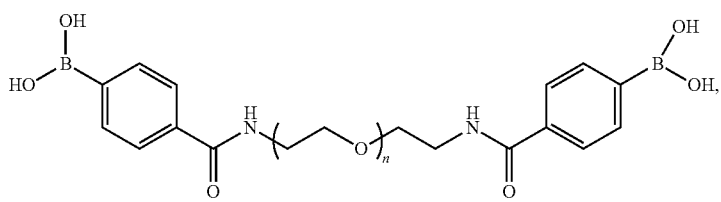

wherein n is from 1 to 100.

In some such embodiments, n is 10 to 50; optionally, n is about 23.

In certain embodiments, the tetrahedral borate ester group covalently bonding the macromonomers to the cross-linkers has the structure:

-continued

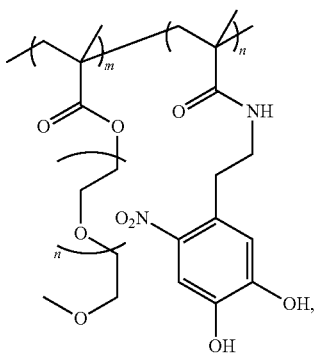

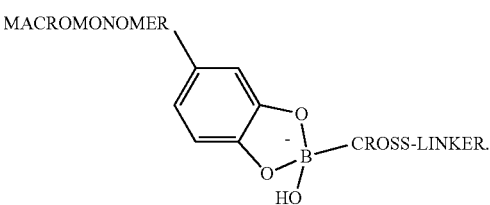

In a second aspect, the disclosure encompasses a cross-linked polymer made by contacting a plurality of macromonomers comprising at least four terminal catechol moieties and having a molecular weight of between 1,000 and 20,000 Daltons with one or more cross-linkers comprising two terminal boronic acid moieties, whereby the macromonomers are cross-linked into a network. In some embodiments, the macromonomers have a molecular weight of 5,000 to 15,000 Daltons.

In certain embodiments, the macromonomers are polyethylene glycols or (dihydroxyphenyl)ethyl methacrylamide copolymers. In some such embodiments, the polyethylene glycols are 4-arm polyethylene glycols wherein each arm is terminated with a catechol moiety. Optionally, the 4-arm polyethylene glycols have the structure:

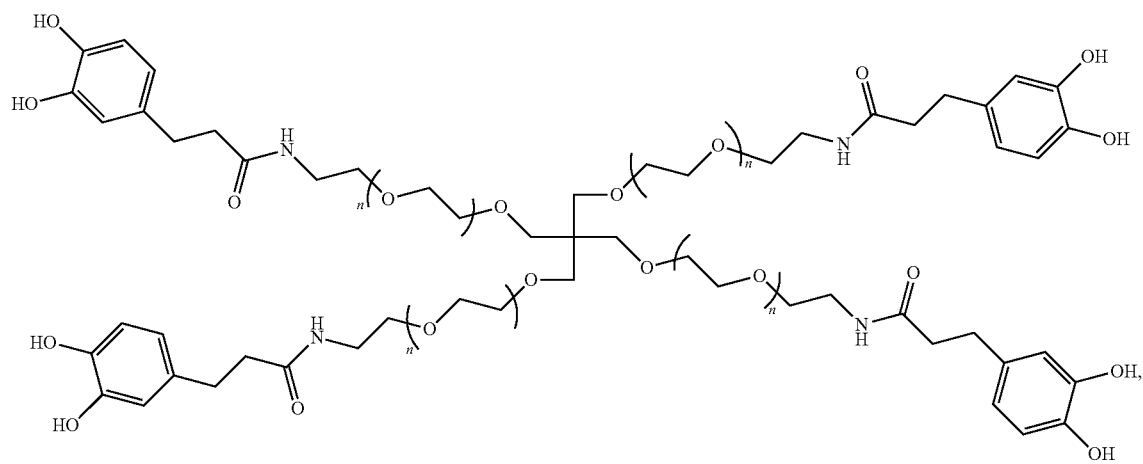

wherein each n is independently selected to be from 1 to 200.

In other such embodiments, the (dihydroxyphenyl)ethyl methacrylamide copolymers are comprised of (dihydroxyphenyl)ethyl methacrylamide monomers wherein the phenyl group is nitro substituted. Optionally, the (dihydroxyphenyl)ethyl methacrylamide copolymers may have the structure:

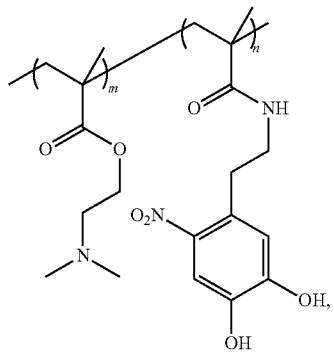

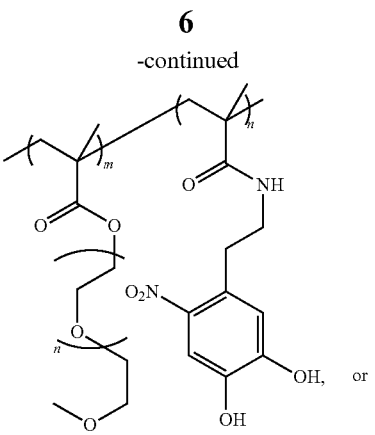

-continued

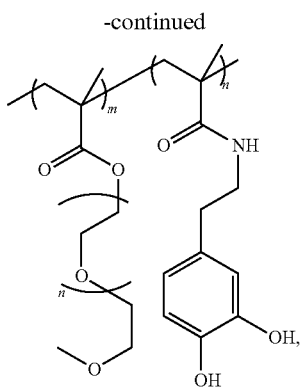

wherein each of m, n and a are independently selected to be from 1 to 200.

In certain embodiments, the two terminal boronic acid moieties on the cross-linkers are attached to an aromatic ring. In such embodiments, the two terminal boronic acid moieties on the cross linkers may be attached to the same aromatic ring or to two different aromatic rings on opposite ends of the cross-linkers.

In certain embodiments, the cross-linkers have the structure:

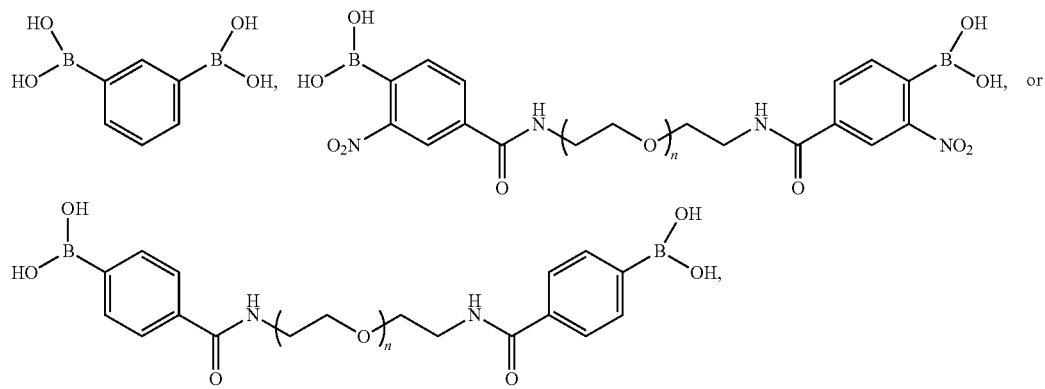

wherein n is from 1 to 100.
In some such embodiments, n is 10 to 50; optionally, n is about 23.

The disclosure further encompasses biocompatible pH-responsive self-healing hydrogels made from the disclosed cross-linked polymers.

In a third aspect, the disclosure encompasses a method of making a pH-responsive self-healing hydrogel. The method includes the step of cross-linking within an aqueous solution a plurality of macromonomers comprising at least four terminal catechol moieties and having a molecular weight of 1,000 to 20,000 Daltons by contacting the macromonomers with one or more cross-linkers comprising two terminal boronic acid moieties. In some embodiments, the macromonomers have a molecular weight of 5,000 to 15,000 Daltons.

In certain embodiments, the macromonomers are polyethylene glycols or (dihydroxyphenyl)ethyl methacrylamide copolymers. Optionally, the polyethylene glycols are 4-arm polyethylene glycols wherein each arm is terminated with a catechol moiety. A non-limiting example of such a 4-arm polyethylene glycol is represented by the structure:

wherein each n is independently selected to be from 1 to 200.

In certain embodiments, the (dihydroxyphenyl)ethyl methacrylamide copolymers are comprised of (dihydroxyphenyl)ethyl methacrylamide monomers wherein the phenyl group is nitro substituted.

In certain embodiments, the (dihydroxyphenyl)ethyl methacrylamide copolymers have the structure:

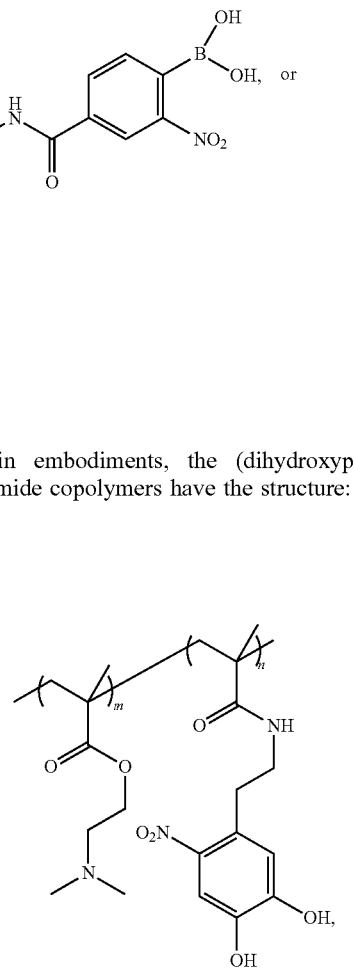

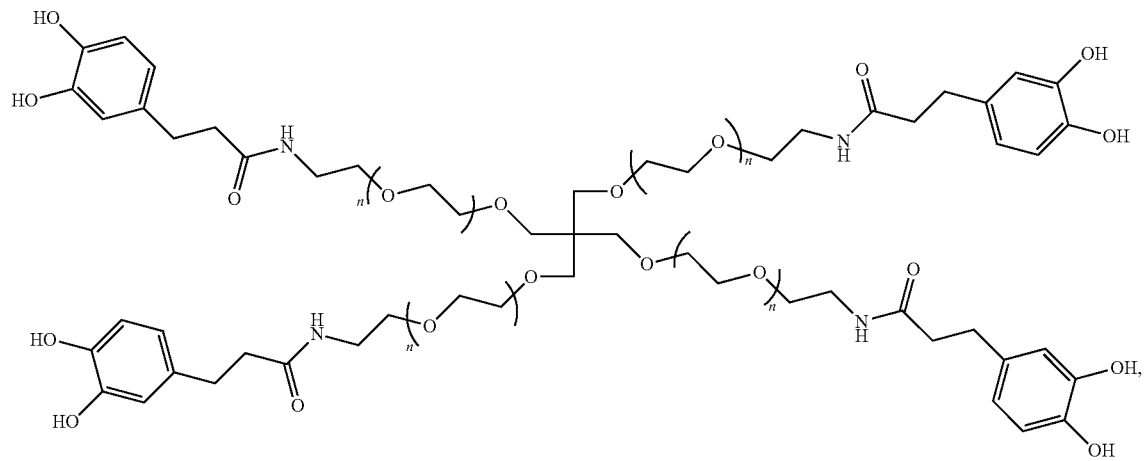

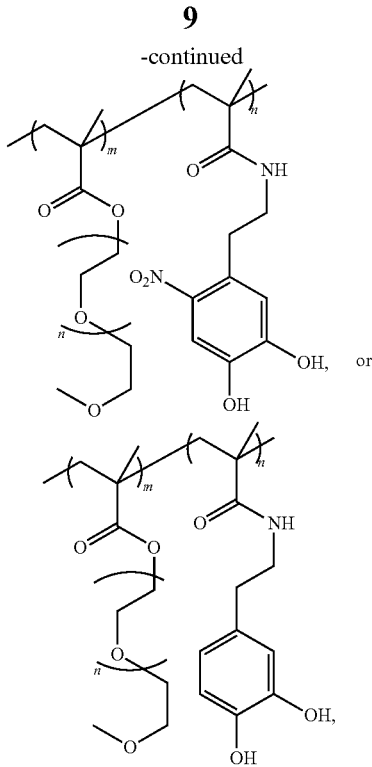

wherein each of m, n and a are independently selected to be from 1 to 200.

In certain embodiments, two terminal boronic acid moieties on the cross-linkers are attached to an aromatic ring. In such embodiments, the two terminal boronic acid moieties on the cross linkers may be either attached to the same aromatic ring or to two different aromatic rings on opposite ends of the cross-linkers.

In certain embodiments, the cross-linkers have the structure:

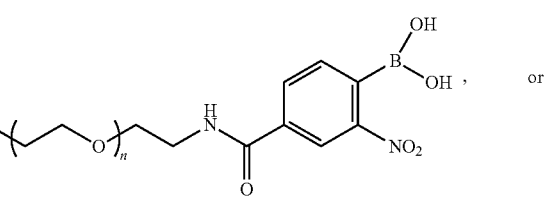

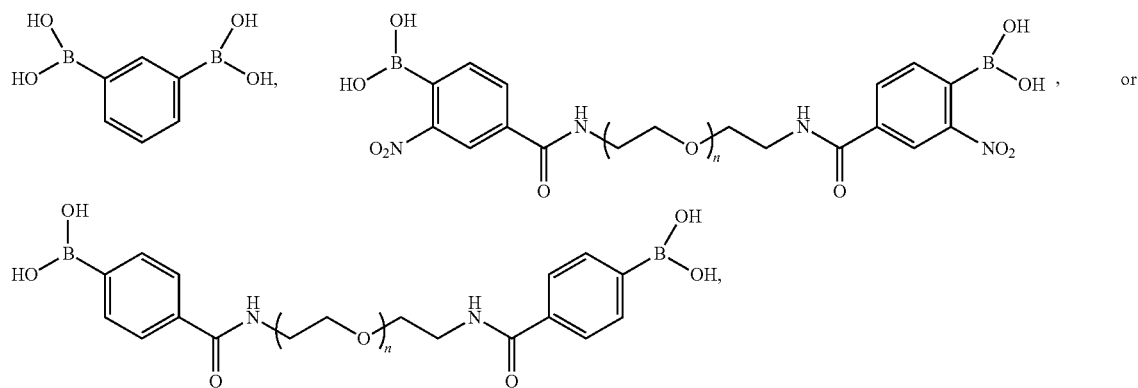

wherein n is from 1 to 100. In some such embodiments, n is from 10 to 50; optionally, n is about 23.

In certain embodiments, the method is performed in an aqueous solution under basic conditions.

In a fourth aspect, the disclosure encompasses the use of the hydrogel as described above in the manufacture of a biomedical product. In certain embodiments, the biomedical product is a carrier for the delivery of therapeutic agents, diagnostic agents, biomaterials, a tissue implant, a cellular growth scaffold, or a surgical tissue adhesive.

DETAILED DESCRIPTION OF THE INVENTION

I. In General

Figure 1:
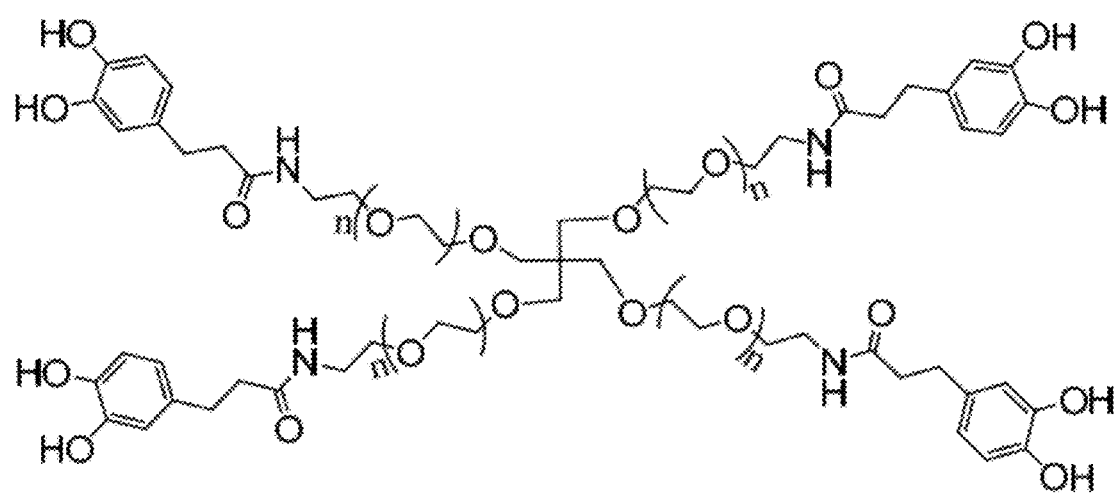
FIG. 1. Molecular structure of 4-arm PEG catechol (cPEG).

In the specification and in the claims, the terms "including" and "comprising" are open-ended terms and should be interpreted to mean "including, but not limited to . . . ." These terms encompass the more restrictive terms "consisting essentially of" and "consisting of." The terms "comprising", "including", "characterized by" and "having" can be used interchangeably.

As used herein and in the appended claims, the singular forms "a", "an", and "the" include the plural reference, unless the context clearly dictates otherwise. As well, the terms "a" (or "an"), "one or more" and "at least one" can be used interchangeably herein.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes, including for describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

While multiple embodiments are disclosed, still other embodiments of the present invention will become apparent to those skilled in the art from the following detailed description. The invention is capable of modifications in various aspects without departing its spirit and scope. Accordingly, the detailed description of the hydrogels of the present invention are to be regarded as illustrative in nature and not restrictive.

II. The Invention

We disclose herein cross-linked polymeric hydrogels formed through the complexation of catechol derivatized macromonomers with certain cross-linkers. The cross-linkers each include at least two boronic acid moieties capable of forming covalent tetrahedral boronate ester bonds when complexed with the catechol moieties of the derivatized macromonomers. The pH-responsiveness of the hydrogels has been characterized, demonstrating covalent gel behavior at alkaline pH and dissociation into a viscous liquid at acidic pH.

To our knowledge, we are the first to report the formation of a hydrogel based on the complexation of a macromonomer catechol with a difunctional boronic acid. This method for hydrogel formation and the hydrogels disclosed herein will have wide applications in the development of commercial biomedical products such as surgery sutures and biomaterials used as tissue replacements, and in the encapsulation of therapeutic cells and drugs.

A. The Hydrogels

The hydrogels disclosed herein are biocompatible, pH responsive, and self-healing. The hydrogels are made when the catechol moieties of the catechol functionalized macromonomers, which have the structure:

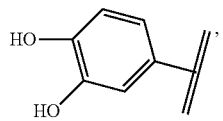

are covalently bonded to the boronic acid moieties of the cross-linker, which have the structure:

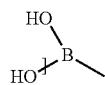

When the catechol moiety of the catechol functionalized macromonomer covalently bonds with the boronic acid moiety of the cross-linker, a covalent tetrahedral boronate ester having the following structure is formed.

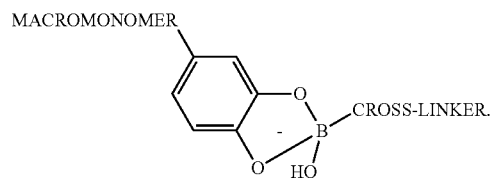

Because the cross-linker has at least two different boronic acid moieties, it can complex with two different catechol functionalized macromonomers, thus facilitating the covalent cross-linking of the catechol functionalized macromonomers to form the disclosed hydrogels. Notably, this complexation reaction takes place under neutral to alkaline conditions, and is reversed in acidic conditions (i.e., is "pH responsive"), as further illustrated in the Examples below. Furthermore, as further illustrated in the Examples below, when the pieces of the disclosed hydrogels are separated through the application of a stress force and subsequently brought back in contact, the hydrogel spontaneously "heals" to reform an undivided gel.

Preferably, the disclosed hydrogels are biocompatible. By "biocompatible," we mean that the hydrogels do not have toxic or injurious effects on biological systems. The hydrogels of the present invention are useful in a wide variety of applications, including, for instance, in medically useful devices or implants that can release bioactive compounds in a controlled manner for local, systemic, or targeted drug delivery; in medically useful devices or implants for use as surgical adhesion prevention barriers, implantable wound dressings, scaffolds for cellular growth for tissue engineering, or as surgical tissue adhesives or sealants; in biomaterials for preventing transplant rejection; and in other medically useful applications such as in hydrogel coatings for preventing bacterial infection of medical device surfaces, and in coatings for chip-based assays of DNA, RNA or proteins.

B. The Catechol Functionalized Macromonomer

The disclosed hydrogels are made from catechol-functionalized macromonomers that are covalently cross-linked in an aqueous solution using one or more cross linkers comprising two or more boronic acid moieties. The macromonomers are large molecules having a molecular weight of 500 to 30,000 Daltons, of 1,000 to 20,000 Daltons, of 2,000 to 15,000 Daltons, of 5,000 to 15,000 Daltons, or of 5,000 to 12,000 Daltons. The macromonomers are functionalized with at least four catechol moieties having the structure:

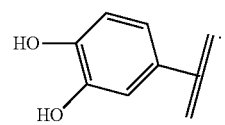

The aromatic ring of the catechol moieties may be unsubstituted (except for the two hydroxyl groups making up the catechol functionality and the attachment of the aromatic ring to the rest of the macromonomer), or may optionally be substituted with additional functional groups. In certain embodiments, the aromatic ring is substituted with an electron withdrawing group, such as a nitro group ($-NO_2$). The catechol moieties readily react with the boronic acid moiety of the cross-linker to form the disclosed hydrogels, particularly under alkaline conditions.

Preferably, the catechol-functionalized macromonomers used to make the disclosed hydrogels are biocompatible. By "biocompatible" we mean a macromonomer that does not have toxic or injurious effects on biological systems and exhibits minimal local inflammatory response in surrounding tissues. For instance, the polyethylene glycol core that is included in several of the exemplary macromonomers disclosed herein is well recognized as being biocompatible, as it is non-immunogenic and resistant to nonspecific protein and cell adhesions. The macromonomers are useful in making hydrogels for use in a wide variety of applications, including, for instance, in tissue repair, in wound healing, in drug delivery, for preventing surgical adhesions, as coatings on medical devices, and in thin adherent hydrogels on biosensors and chip-based diagnostic devices for genomic and proteomic assays.

The catechol-functionalized macromonomers used to make the disclosed hydrogels are designated as "monomers" because they are further complexed together to make the cross-linked polymers that make up the disclosed hydrogels. However, the term "macromonomer" is not limited to what is conventionally considered a monomer. Instead, the prefix "macro" indicates that the term "macromonomer" encompasses large molecules that may themselves be polymers, copolymers, or that may have one or more polymer core.

As non-limiting examples, the catechol-functionalized macromonomers may include polyethylene glycols, (dihydroxyphenyl)ethyl methacrylamide copolymers, and nitro substituted (dihydroxyphenyl)ethyl methacrylamide copolymers.

In certain embodiments, the polymeric core of the catechol-functionalized macromonomers represents 10 to 400 units of polyethylene glycol (PEG), with a total molecular weight (MW) ranging from 500 to 30,000 Da. In other preferred embodiments, the total MW of the polymeric core ranges from about 1,000 to about 20,000 Da. While in certain embodiments, the polymeric core includes PEG, alternative polymeric cores, including but not limited to linear or branched biocompatible polymers that can be similarly functionalized with catechol moieties, may also make up the macromonomers used in making the disclosed hydrogels.

By "functionalized" we mean any linear or branched biocompatible macromonomer modified by including catechol moieties as side chain functional groups or as endgroups. In one embodiment, where PEG comprises the polymeric core of the macromonomer, there are four arms emanating from the center of the macromonomer, with each arm terminating in a catechol moiety. In alternative related embodiments, the polymeric core could comprise six to eight or even ten to twenty different arms emanating from the center of the macromonomer. In another embodiment, the macromonomer is a polymer or copolymer wherein one or more of the monomeric units is functionalized with a catechol moiety. A non-limiting example of such a monomeric unit is a (dihydroxyphenyl)ethyl methacrylamide. A polymer or co-polymer made from such a monomer is another example of an acceptable catechol functionalized macromonomer for making the disclosed hydrogels.

C. The Cross-Linkers

The cross linkers used to make the disclosed hydrogels include two or more boronic acid moieties. In certain preferred embodiments, the boronic acid moieties are attached to aromatic rings. The aromatic rings to which the boronic acid moieties are attached may optionally be substituted with additional functional groups. In certain embodiments, the aromatic ring is substituted with an electron withdrawing group, such as a nitro group ($-NO_2$).

The two or more boronic acid moieties may be attached to the same aromatic ring, as for example, in 1,3-benzendioboronic acid (BDBA), or the boronic acid moieties may be attached to different aromatic rings on the same cross-linker molecule. In embodiments where the boronic acid moieties are attached to different aromatic rings, the aromatic rings may be separated by a linker. The linker may optionally include a polymer core, such as polyethylene glycol. In such embodiments, the polymer core of the linker preferably includes 1-100 monomer units, more preferably, it includes 10-50 monomer units; and most preferably, it includes about 23 monomer units. The polymer core is optionally attached to the boronic acid-containing aromatic rings through an amide linkage.

D. Methods of Synthesis

This disclosure also provides methods of synthesizing the hydrogels described above. In general, the macromonomers are contacted with the cross-linkers in aqueous solution to form covalently cross-linked polymers that formed hydrogels. The reaction takes place in alkaline conditions, and is reversed in acidic conditions, where the polymer dissociates and the hydrogel dissolves.

We further demonstrate herein control of the specific pH of hydrogel dissociation, such that the hydrogel may be formed and maintained under physiological conditions (i.e., pH 7.4). Accordingly, by "alkaline conditions," we mean an environment having a pH of greater than 7.0, which includes the in vivo environment of the human body. By "acidic conditions," we mean an environment having a pH of less than 6.7. Because hydrogel formation can occurs under mild physiological conditions (i.e., pH 7-9), the toxicity to the cells upon exposure to the hydrogel is minimized.

The methods of hydrogel formation described herein provide biocompatible hydrogels that can be modified with bioactive materials to improve the functions of any cells encapsulated by the hydrogels, such as supporting cell growth or supporting the development and secretion of cellular products upon biological stimulus. By "bioactive" we mean a substance that has or causes an effect on or in biological samples. The macromonomers and hydrogels may be functionalized with peptides or other bioactive materials, such as proteins, growth factors, DNA, or RNA.

E. Methods of Use

The biocompatible hydrogels disclosed herein are can be used in a wide variety of medically useful devices and implants. Specifically, the hydrogels may be used in tissue repair, wound healing, drug delivery, in preventing surgical adhesions, as coatings on medical devices, and as thin adherent hydrogels on biosensors and chip-based diagnostic devices for genomic and proteomic assays.

The hydrogels may also be used in medically useful devices or implants that can release bioactive compounds in a controlled manner for local, systemic, or targeted drug delivery. Further, the hydrogels may be used in surgical adhesion prevention barriers, implantable wound dressings, scaffolds for cellular growth for tissue engineering, or as surgical tissue adhesives or sealants.

In certain embodiments, a biological sample may be encapsulated with biomaterials comprising the disclosed hydrogels by reacting the hydrogel with a biomaterial to form a modified hydrogel, and contacting the biological sample with the modified hydrogel, wherein the hydrogel surrounds and encapsulates the sample. By "biological sample" we mean to include a specimen or culture obtained from any source. Biological samples can be obtained from animals (including humans) and may encompass fluids, solids, tissues, and gases. Biological samples include blood products, such as plasma, serum and the like. Such examples are not however to be construed as limiting the sample types applicable to the present invention.

By "biomaterials" we mean materials selected from the group consisting of anti-inflammatory agents, cell function promoting agents, various artificial implants, pacemakers, valves, catheters, and membranes (e.g., a dialyzer), as well as synthetic polymers such as polypropylene oxide (PPO) and polyethylene glycol (PEG).

F. Kits

In further embodiments, a kit for preparing the disclosed hydrogels is provided. In some such embodiments, the kit includes a macromonomer and cross-linker, as described above, and instructions for use.

In certain embodiments, the kit comprises a powdered form of the macromonomer and/or the cross-linker, wherein the powdered macromonomer and/or cross-linker is hydrated by the user for immediate use, such as in a dual syringe device to form a precursor liquid that rapidly gels. Optionally, the kit may contain a solution for dissolving the macromonomer and/or cross-linker.

In other embodiments, the kit comprises at least one of the biocompatible hydrogels as described above, and instructions for use.

In some such embodiments, the kit comprises a powdered form of at least one of the biocompatible hydrogels described above, wherein the powdered hydrogels are hydrated by the user for immediate use, such as in a dual syringe device to form a precursor liquid that rapidly gels. Optionally, the kit may contain a solution for dissolving the hydrogel.

In an alternate embodiment, the kit comprises the disclosed biocompatible hydrogel formulated, delivered and stored for use in physiologic conditions.

By "instructions for use" we mean a publication, a recording, a diagram, or any other medium of expression which is used to communicate the usefulness of the invention for one of the purposes set forth herein. The instructional material of the kit can, for example, be affixed to a container which contains the present invention or be shipped together with a container which contains the invention. Alternatively, the instructional material can be shipped separately from the container or provided on an electronically accessible form on a internet website with the intention that the instructional material and the biocompatible hydrogel be used cooperatively by the recipient.

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. Examples

Example 1

Synthesis of Hydrogel by cPEG Complexation with BDBA

A. Introduction

Figure 2:
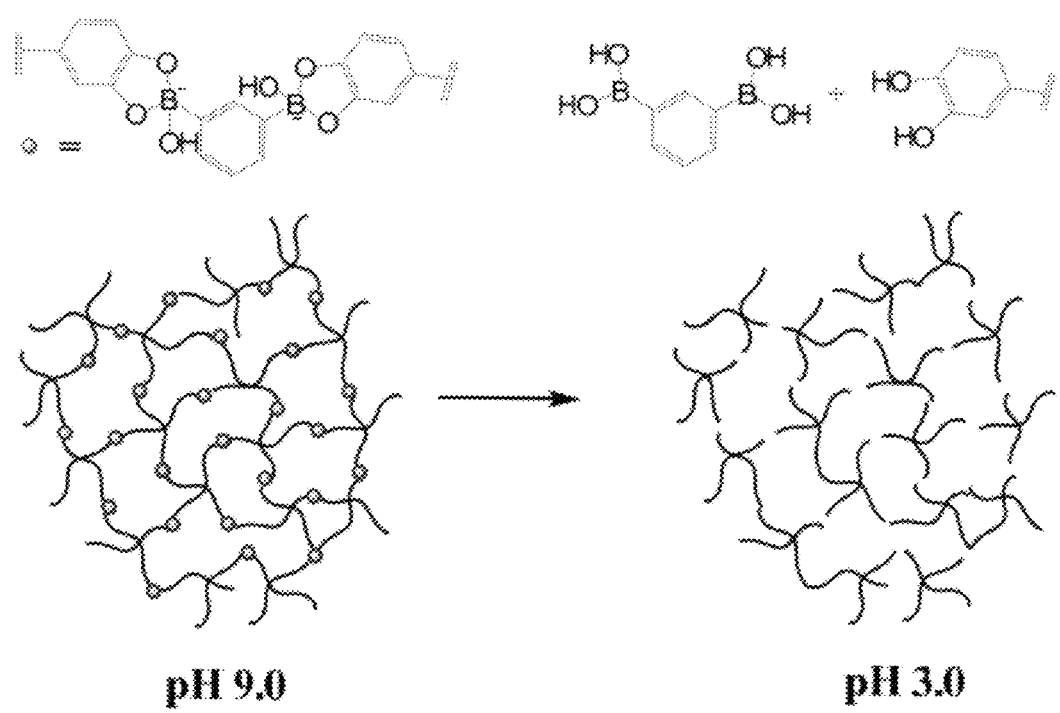
FIG. 2. Schematic illustration of pH-responsive hydrogel based on cPEG and 1,3-benzenediboronic acid in aqueous solution at 20° C.
Figure 3:
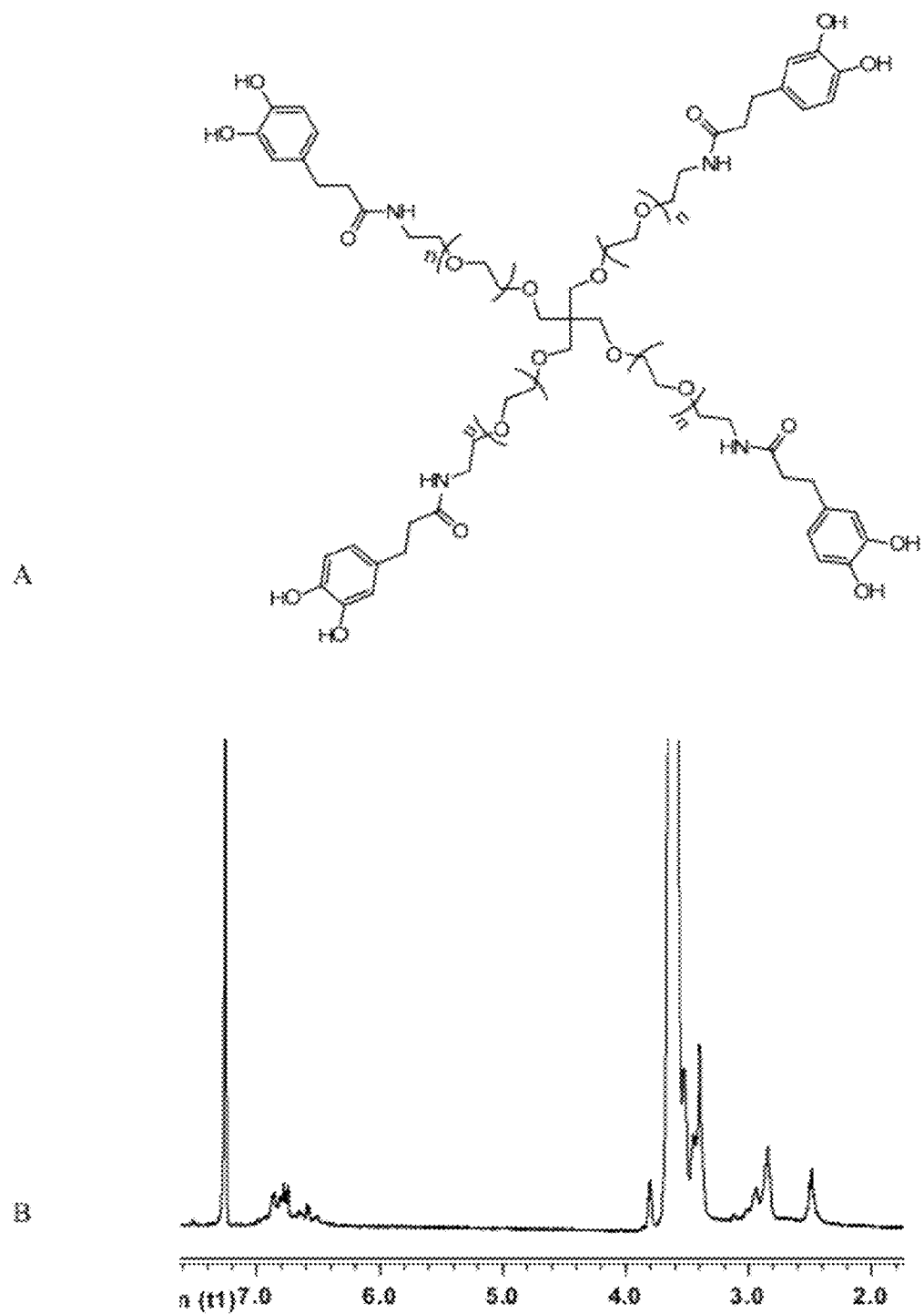
FIG. 3. Structure (A) and $^1$H NMR spectrum of cPEG in $CDCl_3$ (B).
Figure 4:
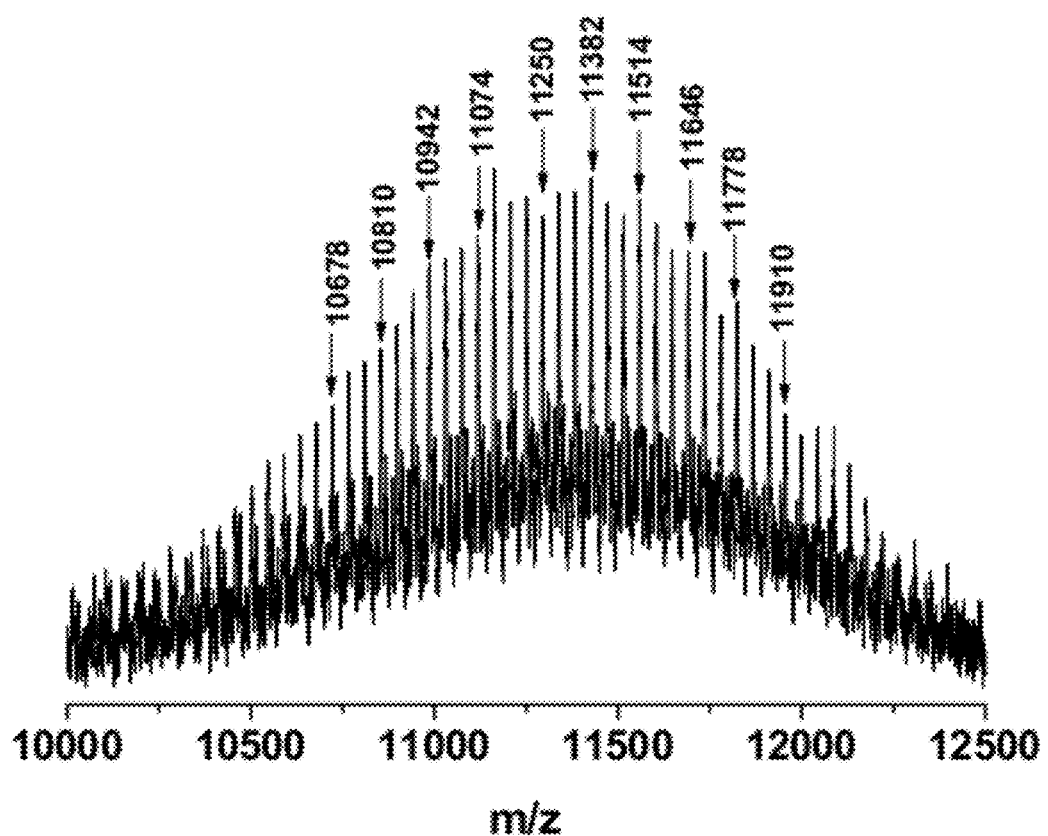
FIG. 4. MALDI-TOF spectrum of cPEG. $M_n$ calculated from software (PolyTools, Bruker) was 11200 g/mol.
Figure 5:
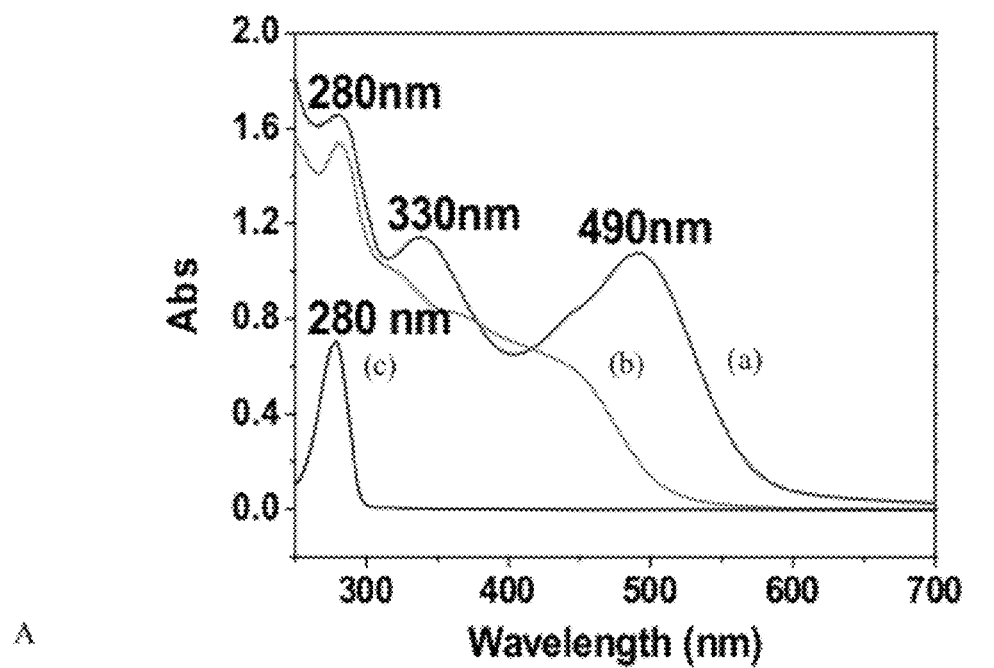
FIG. 5. (A) Uv-vis spectra of mPEG-cat/BDBA at (a) pH 9.0, (b) pH 3.0 and (c) mPEG-cat at pH of 7.4. (B) Hydrogel formed from 7.5 wt % cPEG and BDBA at pH 9.0 and molar ratio of 1:8, and sol produced after the hydrogel shown in B was acidified to pH 3.0.

In this Example, we used cPEG (FIG. 1) as a simple model polymer to construct a hydrogel of the invention (FIG. 2). We chose cPEG because of its branched architecture providing catechol multivalency (FIG. 3), suitable molecular weight (11200 g/mol) (FIG. 4), and the low tissue inflammatory response of cPEG gels. To form gels, solutions of cPEG and BDBA in PBS buffer were mixed at 20° C. and neutralized to alkaline pH. Hydrogels formed within 30 min of mixing at pH 9.0±0.5 (FIG. 5). The pH of 9.0 for complexation was chosen because the pKa of catechol and BDBA are 9.3 and 8.7, respectively, and the optimal pH for complexation is located between the two pKa values.

B. Materials and Methods

Materials.

4-arm PEG amine (Mw 10,000 g/mol) and monofunctional PEG amine (mPEG-NH$_2$, Mw 5,000 g/mol) were purchased from Laysan Bio Inc. 3-(3,4-dihydroxyphenyl) propionic acid (DHPA; Alfa Aesar, 98%), Triethylamine (Aldrich, 99%), N-hydroxybenzotriazole (HOBt, Advanced ChemTech) and O-Benzotriazole-N,N,N',N'-tetramethyl-uronium-hexafluoro-phosphate (HBTU; Novabiochem) were used as received. 1,3-benzenediboronic acid was purchased from Alfa Aesar with purity of 97% and used without further treatment.

Synthesis of cPEG.

In a 50 mL Schlenk flask, 4-arm PEG amine (5.0 g, 2.0 mmol of amine groups, Mw 10,000 g/mol) was dissolved in 45 mL of dichloromethane. 0.73 g (4.0 mmol) DHPA, 0.90 g (6.60 mmol) HOBt, 1.53 g (4.0 mmol) HBTU and 1.0 mL (6.6 mmol) of triethylamine were added sequentially to the PEG solution. Afterwards, 22.5 mL of DMF was added to dissolve the DHPA and this coupling reaction was carried out at 20° C. under N2 atmosphere with continuous stirring for 2.0 h. The crude product was purified by precipitation in diethyl ether (500 mL) once and in methanol (500 mL) three times at −20° C. and in the presence of acetic acid (6.0 mL, 4.0 mmol). The cPEG polymer was vacuum dried after one additional precipitation in diethyl ether. Molecular weight and molecular weight distribution were calculated from MALDI-TOF mass spectrum. (FIG. 4). $^1$H NMR (CDCl$_3$) δ (ppm): 6.5-7.0 (m, 3H, aromatic), 2.85 (s, 2H, —NHCO—CH$_2$—), 2.5 (s, 2H, CH$_2$, adjacent to aromatic), 3.51-3.67 (m, —O—CH$_2$CH$_2$O—).

Synthesis of mPEG-cat.

mPEG-cat was synthesized using a similar method as described above. In a 50 mL Schlenk flask, mPEG amine (3.0 g, 0.6 mmol of amine groups, Mw 5,000 g/mol) was dissolved in 10 mL of dichloromethane. 0.22 g (1.2 mmol) DHPA, 0.27 g (1.98 mmol) HOBt, 0.46 g (1.2 mmol) HBTU and 0.28 mL (1.98 mmol) of triethylamine were added sequentially to the PEG solution. Afterwards, 5.0 mL of DMF was added to dissolve the DHPA and this coupling reaction was carried out at 20° C. under N$_2$ atmosphere with continuous stirring for 2.0 h. The crude product was purified by precipitation in diethyl ether (300 mL) once and in methanol (300 mL) three times at −20° C. and in the presence of acetic acid (1.8 mL, 1.2 mmol). The PEG polymer was vacuum dried after one additional precipitation in diethyl ether. $_1$H NMR (CDCl$_3$) δ (ppm): 6.5-7.0 (m, 3H, aromatic), 2.85 (s, 2H, adjacent to aromatic), 2.5 (s, 2H, —NHCO—CH$_2$—), 3.51-3.67 (m, —O—CH$_2$CH$_2$O—), 3.35 (s, 3H, OCH$_3$).

Formation of Hydrogels.

Hydrogels were prepared by mixing PBS buffer solution of cPEG and BDBA at different molar ratios of catechol to boronic acid. Unless otherwise stated, hydrogels were formed at 15% w/v polymer. A typical procedure used was as follows: In a 1.0 mL vial, 15.0 mg (0.006 mmol catechol) cPEG and 0.05 mL PBS were added to give a clear solution. Then, 0.05 mL of BDBA stock solution (0.024 mmol boronic acid, pH=9.4) was added. The solution mixture was stirred vigorously at 20° C., and a red viscous hydrogel was produced within 30 min. Continued stirring had no apparent impact on gel formation and was determined to be unnecessary for formation of hydrogel.

Characterization.

All $^1$H NMR spectra were recorded on a Varian unity 500 spectrometer in CDCl$_3$ or D$_2$O. $^{11}$B NMR was recorded on a Varian unity 500 spectrometer in D$_2$O with NaOD or D$_2$O with DCl and using boron trifluoride as an external standard. Uv-vis absorption spectra were obtained on a Perkin-Elmer Lambda 1050 Uv-vis spectrometer at room temperature. Rheological measurements were performed in strain-controlled mode on a Paar-Physica MCR 300 rheometer. A cone and plate geometry with a cone diameter of 25 mm and an angle of 2° was employed. The temperature was controlled by the bottom Peltier plate. In each measurement, 0.2 mL of the preformed hydrogel was loaded onto the plate. An evaporation guard was used in combination with damp Kimwipes surrounding the sample to minimize evaporation. Frequency sweeps were performed at 5% constant strain from 0.1 to 100 rad/s at 20° C.

C. Results and Discussion

Figure 6:
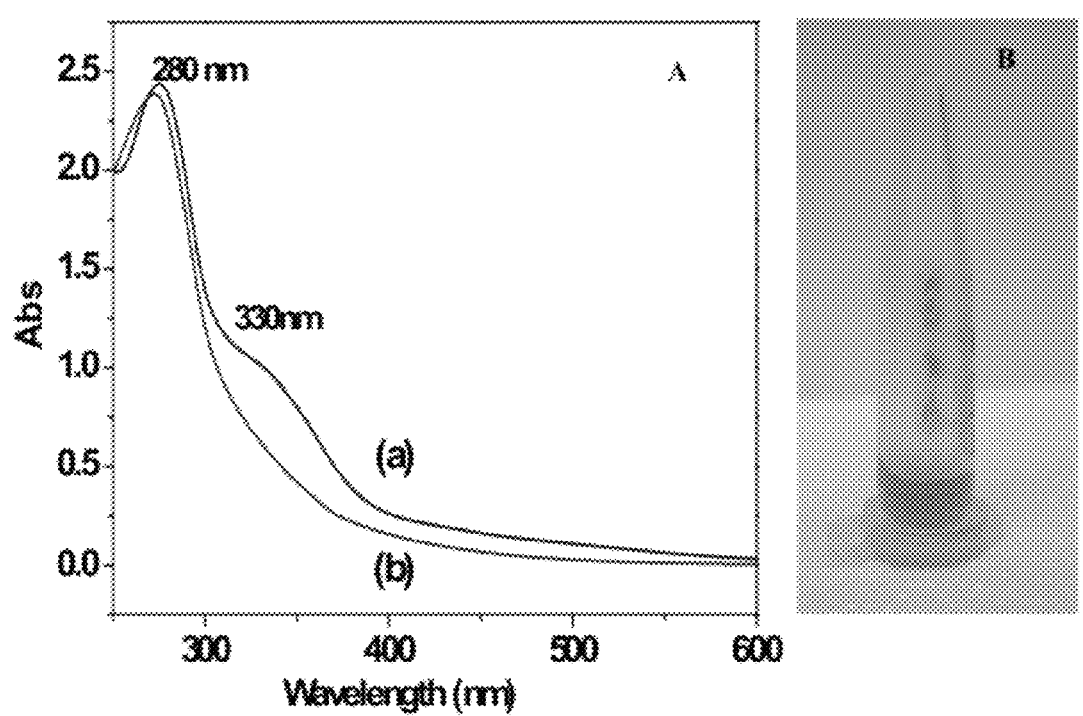
FIG. 6. A: Uv-vis spectrum of mPEG-cat at (a) pH 9.0 and (b) pH 3.0. B: Photo of aqueous solution of cPEG at pH 9.0 after 30 days.

Model uv-vis studies using linear monofunctional PEG-catechol (mPEG-cat; see Materials and Methods for details) with BDBA revealed a large absorption peak at 490 nm resulting from covalent borate ester formation (FIG. 5A), which was distinct from the absorption correlated to catechol oxidation (330 nm peak, FIG. 6). The 490 nm peak disappeared upon reduction of the solution pH to 3.0, indicating dissociation of the borate ester bond. FIG. 5B shows the hydrogel formed from cPEG and BDBA at alkaline pH, and in FIG. 5C its transition to a liquid after adjusting the pH to 3.0 using HCl. The gel to sol transition is accompanied by a color change from red to yellow (color not shown), attributed to dissociation of the borate-catechol complex.

Using similar stoichiometry of borate and catechol, hydrogels were observed to form at polymer concentrations from 5 wt % to 15 wt %. Polymer hydrogels formed in this way are sticky to the touch, which is likely due to the viscoelastic nature of the gels and to the adhesive nature of the catechol.

Due to the stoichiometries of cPEG and BDBA, if the reaction shown in Scheme 2 proceeded to completion, a molar ratio of 1:2 cPEG:BDBA would lead to ideal network cross-linking upon complex formation. However, ideal network formation may not be observed, as the complexation between diols and boronic acid is dynamically reversible and critically depends on solution pH.

A systematic study at pH 9.0 revealed that molar ratio affected hydrogel formation. As indicated in Table 1, when the polymer concentration was held at 15 wt %, red viscoelastic polymer hydrogels were formed in 30 min upon mixing of cPEG and BDBA at molar ratios of 1:6, 1:8, and 1:12 respectively. However, additional BDBA prevented gel formation, as presumably the catechol endgroups became saturated with mono-complexed BDBA, preventing network formation.

TABLE 1

Effect of stoichiometry on gel formation of a 15 wt % solution of cPEG at pH 9.0.

| Molar Ratio[a] | Gelation Time[b] | Physical State |
|---|---|---|
| 1:2 | 7 days | Red gel |
| 1:4 | 2 days | Red gel |
| 1:6 | 0.5 hour | Red gel |
| 1:8 | 0.5 hour | Red gel |
| 1:12 | 0.5 hour | Dark red gel |
| 1:16 | 7 days | Dark brown solution |
| 1:32 | 7 days | Dark brown solution |

[a]cPEG:BDBA.
[b]vial inversion method.

Figure 7:
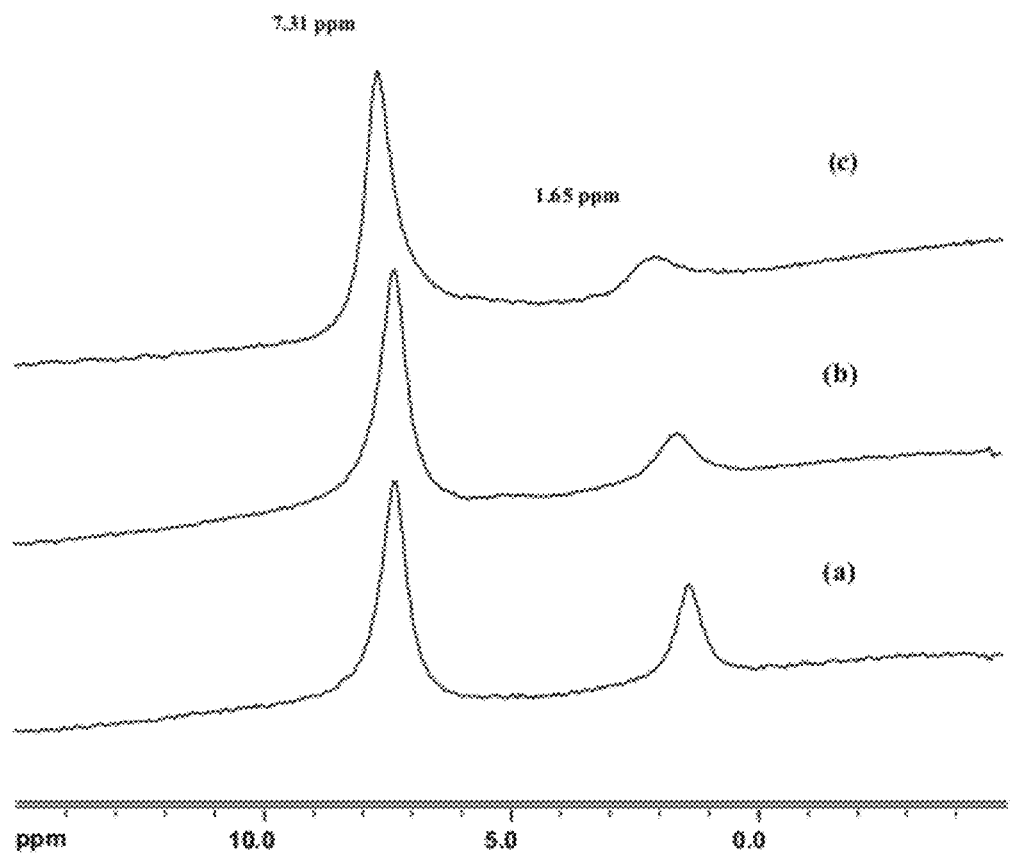
FIG. 7. $^{11}$B NMR spectra of a 2:1 molar ratio of mPEG-cat and BDBA in $D_2O$/NaOD at pH 9.0 after (a) 30 min; (b) 24 h and (c) 48 h.

The complexation between boronate and catechol was further studied by $^1$B and $^1$H NMR using monofunctional mPEG-cat in order to avoid gelation of the solution. As shown in FIG. 7, the $^{11}$B NMR spectrum of a 2:1 mixture of mPEG-cat and BDBA at pH of 9.0 revealed a peak at 1.65 ppm correlating to uncomplexed 1,3-benzenediboronic acid as well as a peak with a chemical shift of 7.31 ppm that is consistent with the formation of the tetrahedral boronate-catechol structure. The peak corresponding to free BDBA decreased with time, suggesting that the complexation of BDBA with catechol occurs gradually, reaching about 80% in 48 hours. It is interesting to note that even after 48 h at ideal stoichiometry (1:2), free uncomplexed BDBA can be detected in the mixture. This we attribute partially to the dynamic nature of the boronate-catechol complex, which fluctuates between the complexed and dissociated states and does not contribute to elastic network formation in the dissociated state. This dynamic behavior has implications for self-healing performance, as discussed below.

Figure 8:
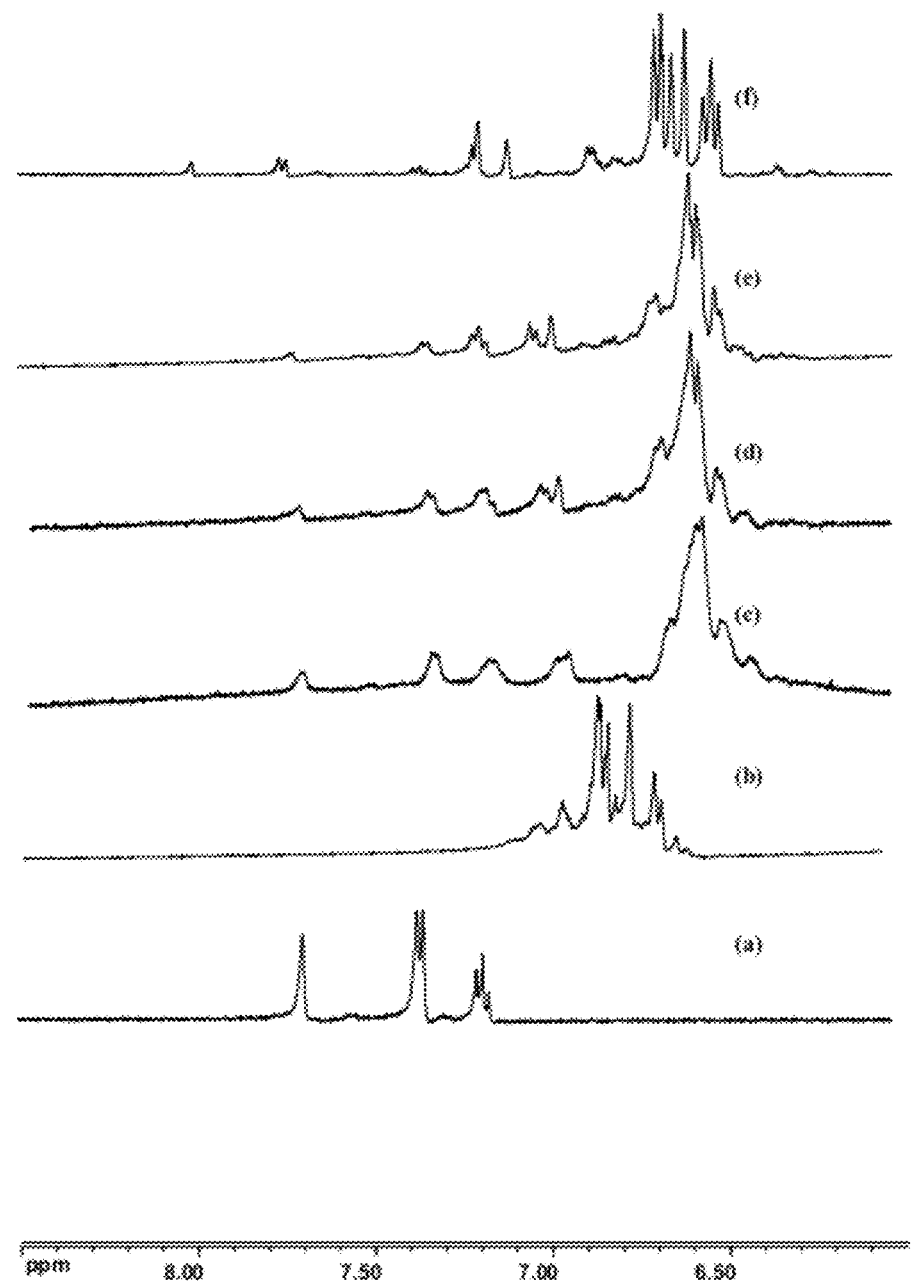
FIG. 8. $^1$H NMR spectra of (a) BDBA in $D_2O$/NaOD at pH 9.0; (b) mPEG-cat at pH 9.0; (c) mPEG-cat/BDBA in $D_2O$/NaOD at pH 9.0 after 30 min, (d) 24 h and (e) 48 h; (f) Solution of (e) after addition of DCl to pH 3.0. Experimental conditions: 15% mPEG-cat. The water peak at 4.8 ppm was used as chemical shift standard.

$^1$H NMR studies confirmed mPEG-cat/complex formation as indicated in FIG. 8, where the three protons from BDBA which have chemical shifts of 7.0-7.6 decreased sharply during the first 30 min after mixing with mPEG-cat, indicating complexation between catechol and boronic acid. Here as well, the conversion of free to complexed BDBA occurred gradually over the first 48 h and was accompanied by a decrease in the chemical shift of boronic acid protons.

Like most of the boronic acid, the chemical shifts of the catechol protons were observed to change upon complex formation. The aromatic protons of catechol (chemical shift 6.5-7.0 ppm in D$_2$O at pH 7) were broadened upon complex formation, and narrowed again upon complex dissociation in acid.

Figure 9:
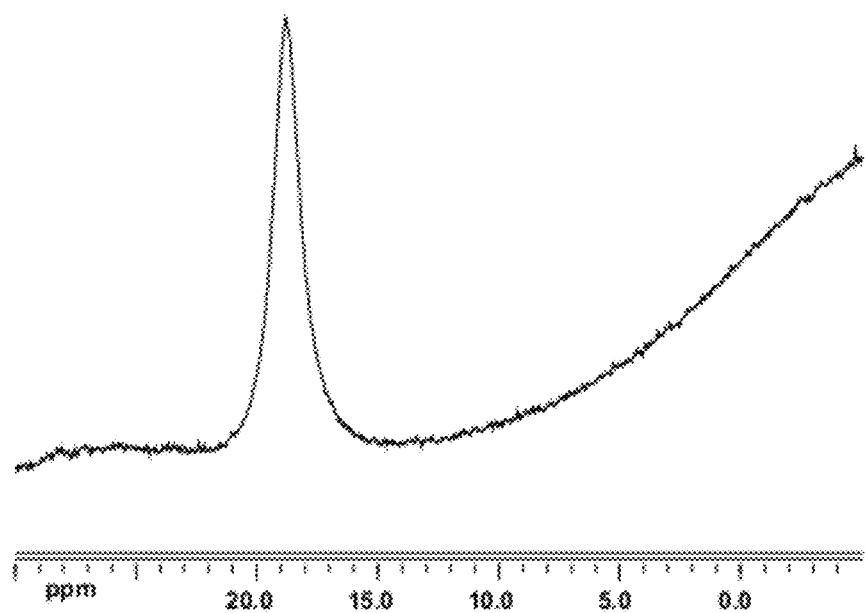
FIG. 9. $^{11}$B NMR spectrum of mPEG-cat/BDBA mixture at pH 3.0. The solution resulted from acidification of the gel formed from mPEG-cat and BDBA at molar ratio of 2:1 (mPEG-cat:BDBA), pH 9.0 in $D_2O$/NaOD for 48 h.
Figure 10:
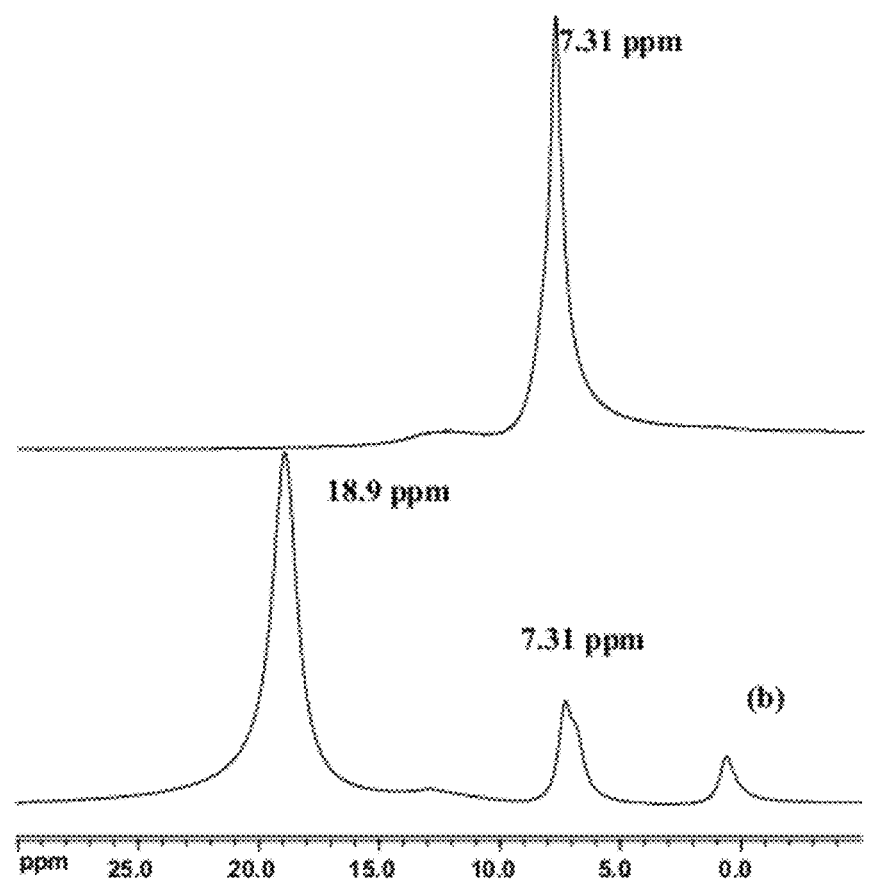
FIG. 10. $^{11}$B NMR spectrum of Borax/dopamine with molar ratio of 1:1 at pH 9.0 (a) and pH 3.0 (b).
Figure 11:
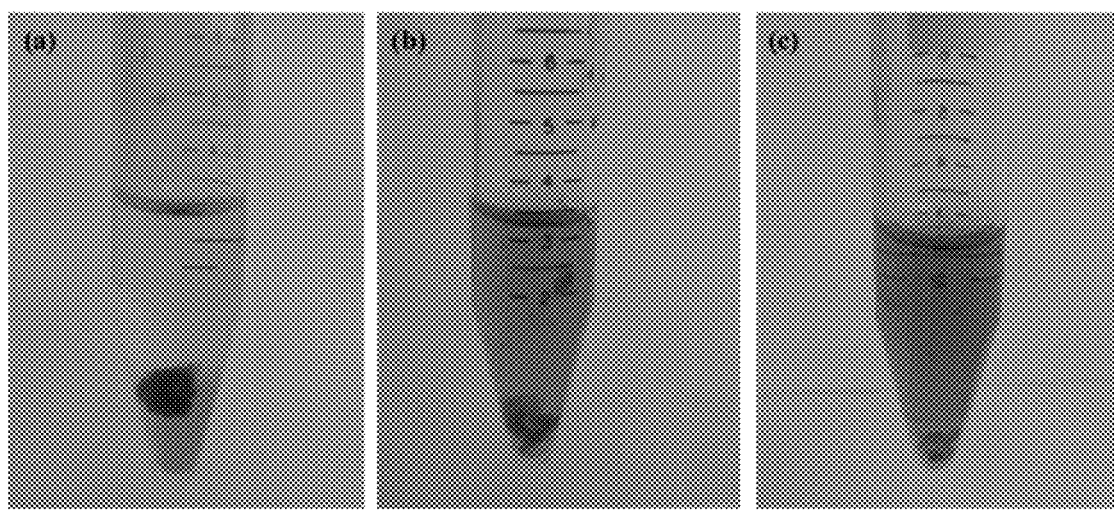
FIG. 11. Stability of hydrogel formed from cPEG and BDBA in PBS buffer at pH 7.4 and 37° C. Photographs were taken at 20 min (a), 1.5 h (b) and (c) 17 h. The molar ratio of cPEG to BDBA was 1:8.

Proton signals from boronic acid were not straightforward to detect or interpret at pH 3.0, due to the limited solubility of BDBA under these conditions. However, acidification of the gel formed by cPEG and BDBA after 48 hours at pH 9.0 and analysis by $^{11}$B NMR revealed the disappearance of the 7.31 ppm peak associated with the boronate-catechol complex, and simultaneous reappearance of the 18.9 ppm peak attributed to free borate (FIG. 9). This peak assignment was confirmed by $^{11}$B NMR spectrum of borax/dopamine at pH 3.0 (FIG. 10). Gels formed at pH 9.0 and then immersed in pH 7.4 buffer dissolved over a period of several hours (FIG. 11).

Figure 12:
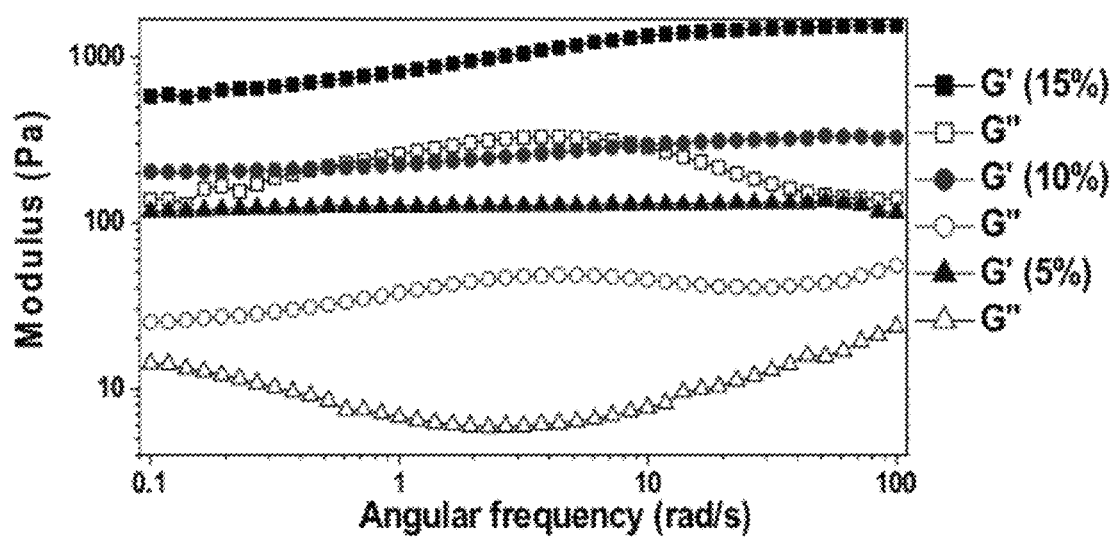
FIG. 12. Dynamic frequency sweep of hydrogels formed from BDBA and cPEG with polymer concentration of (a) 15 wt % (b) 10 wt % and (c) 5.0 wt %. The molar ratio of cPEG to BDBA was 1:8 for each concentration.
Figure 13:
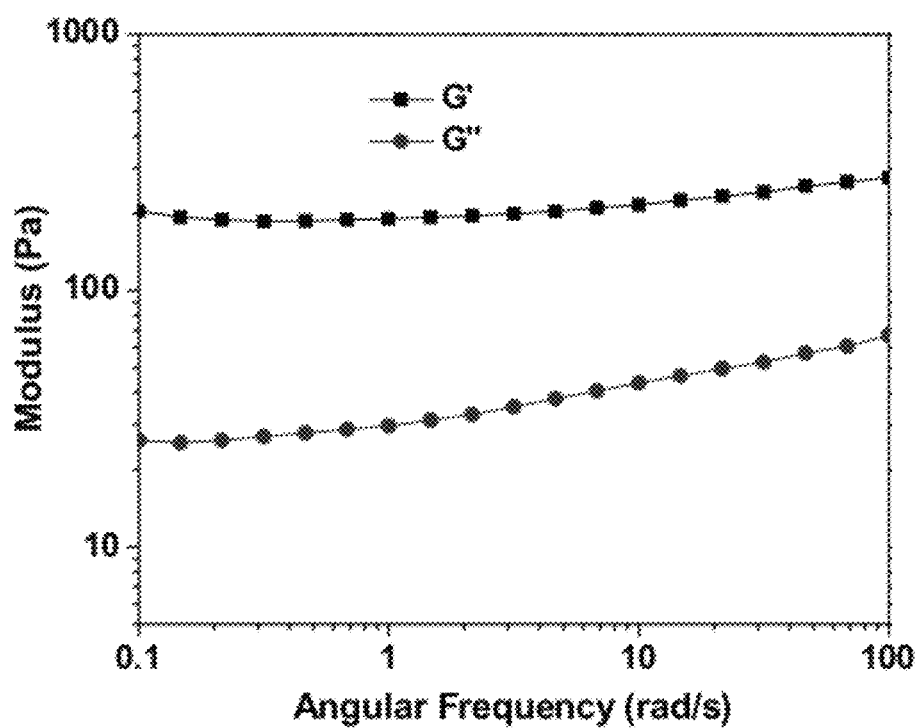
FIG. 13. Dynamic frequency sweep of hydrogels formed from BDBA and cPEG with polymer concentration of 15 wt % at 37° C. The molar ratio of cPEG to BDBA was 1:8.

Rheological studies of the cPEG/BDBA gels were consistent with covalently cross-linked hydrogels, exhibiting storage moduli greater than loss moduli across a wide frequency range, and little change in storage modulus with frequency (FIG. 12). Storage modulus was concentration dependent within the range 5-15 wt % cPEG, with a maximum observed storage modulus of approximately 1500 Pa (15 wt %). The storage modulus at 37° C. was lower than at 20° C. (FIG. 13).

Figure 14:
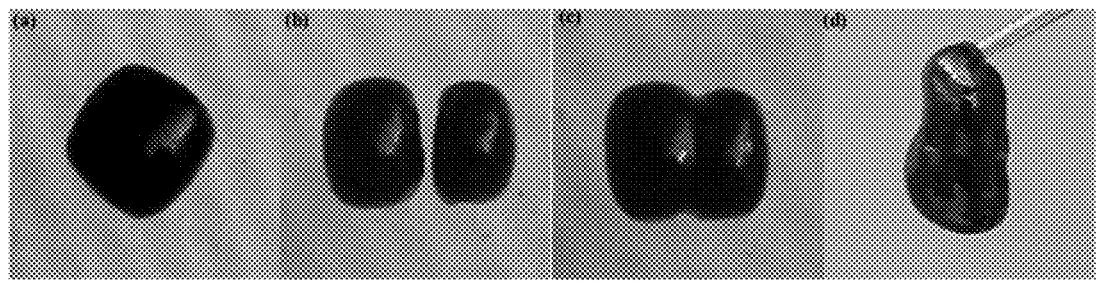
FIG. 14. Self-healing properties of the covalent polymer gel formed from cPEG (15 wt %) and BDBA at pH 9.0. The gel was formed into a cube (a), cut into two pieces (b), fused together (c), and then stretched without fracture 30 s after fusion (d). The molar ratio of cPEG to BDBA was 1:8.

Interestingly, hydrogels prepared in this way are sticky to the touch and possess self-healing ability. As depicted in FIG. 14, a cube of 15 wt % hydrogel was cut into two pieces and then brought back together at the fracture surfaces. The two pieces of fractured gel healed autonomously and rapidly by simply contacting the fractured surfaces together (FIGS. 14b and 14c). No obvious border was seen between the connected gels after fusion, and the joint between the two parts of the healed gel was strong enough to be stretched without fracturing 30 seconds after fusion (FIG. 14d). This observation was repeatable and effective wherever the cut was made or the gels were fused.

Figure 15:
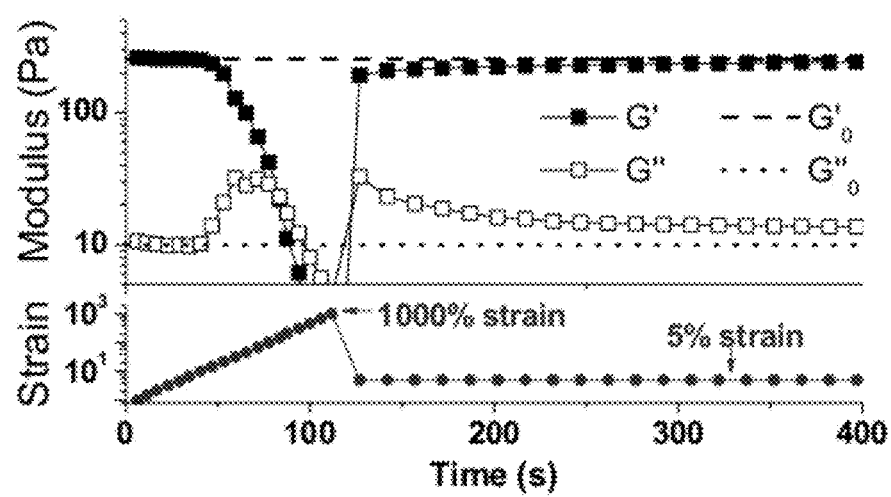
FIG. 15. Time-dependent self-healing of gel after failure. The moduli of the gel before fracture are indicated by $G'_0$ and $G''_0$. The gel was fractured under large strain (1000%, 10 rad/s; 20° C.) and then the recovery moduli $G'$ and $G''$ were monitored at 5% strain. The molar ratio of cPEG to BDBA was 1:8 and polymer concentration was 15 wt %.

FIG. 15 demonstrates this self-healing property by oscillatory rheology. In this experiment the gel was first strained up to 1000%, resulting in gel failure. Following this, the time-dependent recovery was monitored at 5% strain and 10 rads/s, revealing mechanical recovery of the storage modulus (G') on the minute time scale.

We believe the self-healing mechanism is mainly attributable to the dynamically reversible complexation between boronic acid and catechol. The $^{11}$B NMR supports the availability of free 1,3-benzendioboronic acid under conditions where gel is formed, implying a dynamic equilibrium between free and complexed borate that could contribute to the self-healing mechanism. Upon return of fractured surfaces together, free BDBA and catechol functional groups should be capable of complexing with each other at the interface to reform the network. Covalent reactions may also contribute to healing the interface, as the catechol is known to undergo oxidative coupling under basic conditions. However, we do not have any direct evidence for this effect at this time.

D. Conclusion

In conclusion, novel covalent hydrogels were produced by complexation of a multifunctional catechol polymer with a bifunctional borate compound. The dynamic nature of the boronate ester linkages gave rise to self-healing hydrogels exhibiting high stability at alkaline pH and low stability under acidic conditions. This strategy for hydrogel formation may be used in various biomedical applications.

Example 2

Synthesis of Hydrogel by PDMA-co-PNDHPMA or POEGMA-co-PNDHPMA Complexation with NPBA-PEG-NPBA or PBA-PEG-PBA A. Introduction In Example 1 above, we reported the formation of pH-responsive hydrogels which were cross-linked by complexation of 1,3-benzenediboronic acid and a 4-arm PEG catechol (cPEG) under basic conditions. Due to the relatively high pKa of catechol (9.3), the hydrogels prepared in Example 1 may have limited applications under physiological condition (i.e., pH of 7.4). In this Example, we demonstrate the synthesis of pH-responsive, self-healing hydrogels at physiological pH in aqueous solution.

Figure 16:
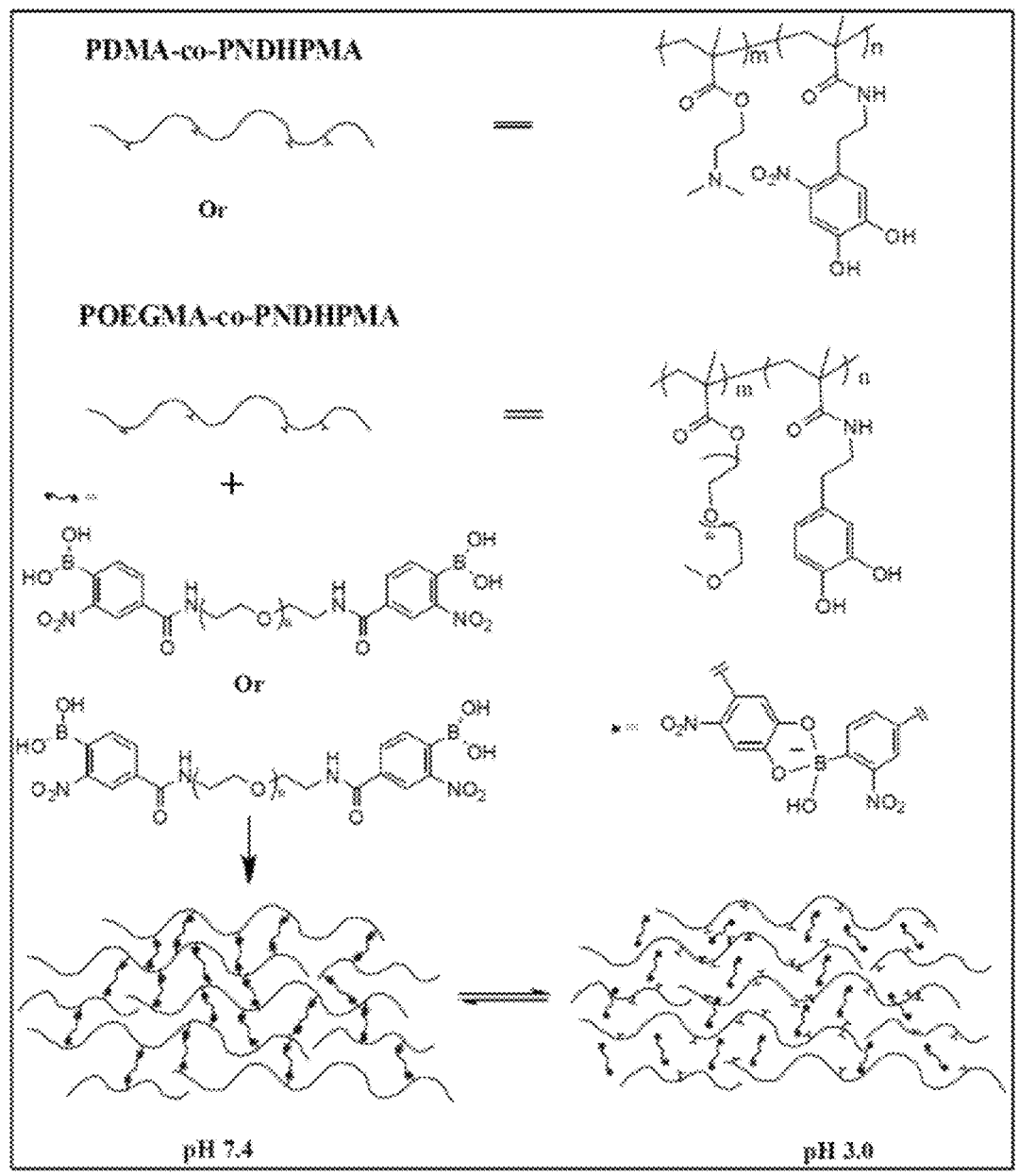
FIG. 16. Schematic illustration of pH-responsive hydrogel based on complexation of nitro-catechol containing statistical copolymer PDMA-co-PNDHPMA or POEGMA-co-PNDHPMA, and cross-linker NPBA-PEG-NPBA or PBA-PEG-PBA.

The hydrogels are made by complexing a nitro-substituted catechol-containing copolymer with a polyethylene glycol-based cross-linker having a terminal phenylboronic acid moiety at each end. Specifically, a statistical copolymer containing nitro-substituted catechol, poly(N,N'-dimethylamino ethyl methacrylate)-co-poly(6-nitro-2-(3,4-dihydroxy-6-nitrophenyl)ethyl methacrylamide) (PDMA-co-PNDHPMA), and a cross-linker containing nitro-substituted phenylboronic acid, 3-nitro-4-phenylboronic acid PEG 3-nitro-4-phenylboronic acid (NPBA-PEG-NPBA), were designed and synthesized for this hydrogel system (see FIG. 16). The chemically cross-linked hydrogels are dynamically reversible, dissociable at acidic conditions, and also possess self-healing and antibacterial property.

B. Materials and Methods

Materials. Monofunctional PEG carboxylic acid (mPEG-COOH, $M_w$~5,000 g/mol) and difunctional PEG amine ($NH_2$-PEG-$NH_2$, $M_w$~1,000 g/mol) were purchased from Laysan Bio Inc. Triethylamine (Aldrich, 99%), N-hydroxybenzotriazole (HOBt, Advanced ChemTech) and O-Benzotriazole-N,N,N',N'-tetramethyl-uronium-hexafluoro-phosphate (HBTU; Novabiochem) were used as received. 4-carboxy-2-nitrophenylboronic acid and 4-carboxyphenylboronic acid was purchased from AOBChem with purity of 98% and used directly. 2-(Dimethylamino) ethyl methacrylate (DMA, Aldrich, 98%) was distilled under vacuum prior to use. Sodium nitrite (Aldrich, 99%) and mechacryloyl chloride (Aldrich, 97%) were used as received. Oligo ethylene glycol methacrylate (OEGMA, Mw~300 g/mol) was passed over basic alumina prior to use.

Synthesis of mPEG Nitro-Catechol (mPEG-Ncat).

mPEG-COOH (2.0 g, 0.4 mmol of carboxylic acid groups, $M_w$~5,000 g/mol) was dissolved in 5.0 mL of dichloromethane. 0.24 g (0.8 mmol) nitro-substitute dopamine, 0.42 g (0.8 mmol) PyBop, and 0.20 mL (1.2 mmol) of N,N-Diisopropylethylamine (DIPEA) were added sequentially to PEG solution. Afterwards, 10.0 mL of dimethydulfoxide (DMSO) was added to give a clear solution. This coupling reaction was carried out at 20° C. under $N_2$ atmosphere with continuous stirring for 2.0 h. The crude product was purified by precipitation in diethyl ether (400 mL) once and in methanol (300 mL) three times at −20° C. and in the presence of acetic acid (1.2 mL, 0.8 mmol). The PEG polymer was vacuum dried after one additional precipitation in diethyl ether. $^1$H NMR (CDCl$_3$) δ (ppm): 7.68 (m, 1H, aromatic adjacent to NO$_2$), 6.81 (m, 1H, aromatic), 3.1 (s, 2H, —CO—NH—CH$_2$—CH$_2$—), 3.96 (s, 2H, —CO—NH—CH$_2$—CH$_2$—), 3.51-3.67 (m, —O—CH$_2$CH$_2$O—), 3.35 (s, 3H, —OCH$_3$).

Synthesis of 2-(3,4-Dihydroxy-6-Nitrophenyl)Ethyl Methacrylamide: Nitro Substituted DHPMA Monomer (NDHPMA).

To a 1000 mL two neck round bottom flask, nitro-dopamine sulfuric acid (7.6 g, 25.6 mmol), 350 mL deionized water and borax (20.0 g, 51.2 mmol) were added. This mixture solution was degassed by bubbling with argon for 30 min and pH was adjusted with Na$_2$CO$_3$ to 9.0. Mechacryloyl chloride (4.0 mL, 31.0 mmol) was added dropwise in 10 min. Reaction was carried out at 0° C. for 3.0 h under argon atmosphere and pH was sustained around 9 throughout the reaction. The pH of the resulting dark solution was changed to around 3 using HCl. This water solution was washed with ethyl acetate 3 times (80 mL×3). The organic layer was collected, dried with anhydrous sodium sulfate. Nitro-substituted monomer was purified by recrystallization in ethyl acetate. $^1$H NMR (DMSO) δ (ppm): 5.54; 5.28 (s, 1H, protons from double bond), 1.98 (s, 3H, —CH$_3$), 8.0 (s, 1H, —CO—NH), 4.01 (s, 2H, —NH—CH$_2$), 2.95 (s, 2H, —NH—CH$_2$—CH$_2$—), 6.68 (s, 1H, aromatic), 7.48 (s, 1H, aromatic adjacent to NO$_2$), 9.84, 10.38 (s, 1H, —OH).

Synthesis of 2-(3,4-Dihydroxyphenyl)Ethyl Methacrylamide: DHPMA Monomer.

To a 1000 mL two neck round bottom flask, dopamine (14.7 g), 350 mL deionized water and borax (57.2 g) were added. This mixture solution was degassed by bubbling with argon for 30 min and pH was adjusted with $NaCO_3$ to 9.0. Mechacryloyl chloride (9.0 mL) was added dropwise in 10 min. Reaction was carried out at 0° C. for 3.0 h under argon atmosphere and pH was sustained around 9 throughout the reaction. The pH of resulted solution was changed to around 3.0 using HCl. This water solution was washed with ethyl acetate 3 times (80 mL×3). The organic layer was collected, dried with anhydrous sodium sulfate. Monomer was purified by recrystallization in ethyl acetate. $^1$H NMR (DMSO) δ (ppm): 5.6; 5.3 (s, 1H, protons from double bond), 1.83 (s, 3H, —$CH_3$), 8.0 (s, 1H, —CO—NH), 3.2 (s, 2H, —NH—$CH_2$), 2.54 (s, 2H, —NH—$CH_2$—$CH_2$—), 6.43, 6.56, 6.63 (s, 1H, aromatic), 8.76, 8.64 (s, 1H, —OH).

Synthesis of 6-Nitro Dopamine (N-Dopamine).

20% $H_2SO_4$ (25 mL) was added dropwise to a solution of dopamine hydrochloride (5.0 g, 26.4 mmol) and sodium nitrite (6.3 g, 91.3 mmol) in water (150 mL) cooled in a ice bath. The addition of $H_2SO_4$ was finished in 10 min and the reaction was stopped after 2.0 h. The reduced dark-yellow solution with insoluble products was filtered, followed with washing with water (65 mL) and methanol (100 mL). The yellow product was vacuum-dried with a yield of 70.8%. $^1$H NMR (DMSO) δ (ppm): 7.46 (s, 1H, aromatic adjacent to $NO_2$), 6.61 (s, 1H, aromatic), 3.04 (s, 4H, —$CH_2$—$CH_2$—$NH_2$).

Synthesis of 3-Nitro-4-Phenylboronic Acid PEG 3-Nitro-4-Phenylboronic Acid (NPBA-PEG-NPBA).

4-carboxy-2-nitrophenylboronic acid (1.27 g, 6.0 mmol), $NH_2$-PEG-$NH_2$ ($M_w$~1000 g/mol, 2.0 g, 4.0 mmol amine), Bop (2.65 g, 6.0 mmol), and DIPEA (2.0 ml, 12 mmol) were dissolved in mixture solvent of DCM (10 ml) and DMF (5.0 ml). The reaction was performed at 20° C. under argon atmosphere for 2.0 h with continuous stirring. The reaction solution was precipitated in ether (400 mL) and yellow solid product was produced. This product was dissolved in ethanol and precipitated three times in freezer at −20° C. for 3 hours and collected by centrifuge followed with vacuum drying treatment with a yield of 67%. $^1$H NMR (MeOD-$d_4$) δ (ppm): 8.70 (s, 1H, aromatic adjacent to $NO_2$), 8.21 (s, 1H, aromatic adjacent to —CO—), 7.65 (s, 1H, aromatic adjacent to —$B(OH)_2$), 3.63 (m, PEG).

Synthesis of 4-Phenylboronic Acid PEG 4-Phenylboronic Acid (PBA-PEG-PBA).

4-carboxy-phenylboronic acid (0.5 g, 3.0 mmol), $NH_2$-PEG-$NH_2$ ($M_w$~1000 g/mol, 1.0 g, 2.0 mmol amine), Bop (1.32 g, 3.0 mmol), and DIPEA (1.0 ml, 6 mmol) were dissolved in mixture solvent of DCM (10 ml) and DMF (5.0 ml). The reaction was performed at 20° C. under argon atmosphere for 2.0 h with continuous stirring. The reaction solution was precipitated in ether (400 mL) and yellow solid product was produced. This product was dissolved in ethanol and precipitated three times in freezer at −20° C. for 3 hours and collected by centrifuge followed with vacuum drying treatment with a yield of 67%. $^1$H NMR (MeOD-$d_4$) δ (ppm): 7.7 (d, 2H, aromatic adjacent to —$B(OH)_2$), 7.8 (d, 2H, aromatic adjacent to —CO—), 3.63 (m, EO units).

Synthesis of PDMA-co-PNDHPMA Statistical Copolymer

A typical method for preparation of nitro catechol based random copolymer is as follows. In a 100 mL of schlenk flask was added 2-(dimethylamino)ethyl methacrylate (6.0 g, 0.038 mol), NDHPMA (0.54 g, 2.0 mmol), AIBN (65 mg, 1 wt % of two monomer) and anhydrous DMF (20 mL). The reaction solution was freeze-thaw three times to remove oxygen inside. Reaction was carried out at 60° C. for 24 h with continuous stirring. Conversion of two monomers was determined by $^1$H NMR study of reaction solution. Copolymers were purified by dialysis against methanol at existence of acetic acid. Polymer composition was determined from $^1$H NMR studies. The other statistical copolymer, poly (oligo ethylene glycol methacrylate-co-poly(NDHPMA) (POEGMA-co-PNDHPMA, 10 mol % nitro-catechol), was synthesized using the same protocol described above by using monomer OEGMA, and NDHPMA.

Preparation of Hydrogel

Hydrogels were prepared by mixing PBS buffer solution of PDMA-co-PNDHPMA and NBPA-PEG-NPBA with certain molar ratio of catechol to boronic acid at given polymer concentration. A typical procedure used was as follows: In a 1.0 mL vial was added 45 mg (3.12 mmol catechol) PDMA-co-PNDHPMA (3 mol % nitro-catechol) and 0.3 mL PBS to give a clear solution. Then, 0.08 mL of NPBA-PEG-NPBA stock solution was added, which was prepared in advance (44 mg/mL). Yellow transparent, sticky hydrogel was formed instantly right after this these two solutions are mixed. (15 wt % polymer, molar ratio of nitro-catechol to NBA-PEG-NBA was 1:2).

Characterization.

All $^1$H NMR spectra were recorded on a Varian unity 500 spectrometer in $CDCl_3$, MeOD or $D_2O$. $^{11}$B NMR was recorded on a Varian unity 500 spectrometer in $D_2O$ with NaOD or $D_2O$ with DCl and using boron trifluoride as external standard. Uv-vis absorption spectra were obtained on a Perkin-Elmer Lambda 1050 Uv-vis spectrometer at room temperature. Rheological measurements were performed in strain-controlled mode on a Paar-Physica MCR 300 rheometer. A cone and plate geometry with a cone diameter of 25 mm and an angle of 2° was employed. The temperature was controlled by the bottom Peltier plate. In each measurement, 0.2 mL of the preformed hydrogel was loaded onto the plate. An evaporation guard was used in combination with damp Kimwipes surrounding the sample to minimize evaporation. Frequency sweeps were performed at 5% constant strain from 0.1 to 100 rad/s at 20° C. The molecular weights and polydispersities of the PDMA-co-PNDHPMA statistical copolymers were determined by aqueous GPC at 35° C. using a Shodex SB-804 HQ and a Shodex SB-802.5 HQ connected in series to a Wyatt multi angle light scattering (DAWN HELEOS) and Wyatt Optilab T-rEX refractive index detector. The eluent was a pH 3.5 buffer solution comprising 0.30 M $NaH_2PO_4$ and 1.0 M acetic acid at a flow rate of 1.0 mL min-1. Near-monodisperse PEG standards (Mp) 3930-12140 g mol-1) were used for calibration. The data were analyzed using Astra software (version 5.3.4).

C. Results and Discussion

Water-soluble statistical copolymer, PDMA-co-PNDHPMA, was synthesized by free radical copolymerization of DMA and nitro-substituted monomer, NDHPMA, which was synthesized by reaction of methacryloyl chloride with nitro-substituted dopamine, 6-nitro dopamine, (nitrodopamine), which was synthesized using a previous reported method (Biapolitano et al. *Tetrahydron* 1992, 48, 8515-8522). The copolymer compositions, molar percent of nitro-catechol and DMA, were well tuned by varying molar ratio of two starting monomers. Catechol-containing monomers generally act as inhibitors, because catechols are able to quench free radicals during polymerization. Although the polymerization worked well, the polymers produced have lower molecular weight than the corresponding polymers produced from non-catechol containing monomers under same reaction condition.

Figure 17:
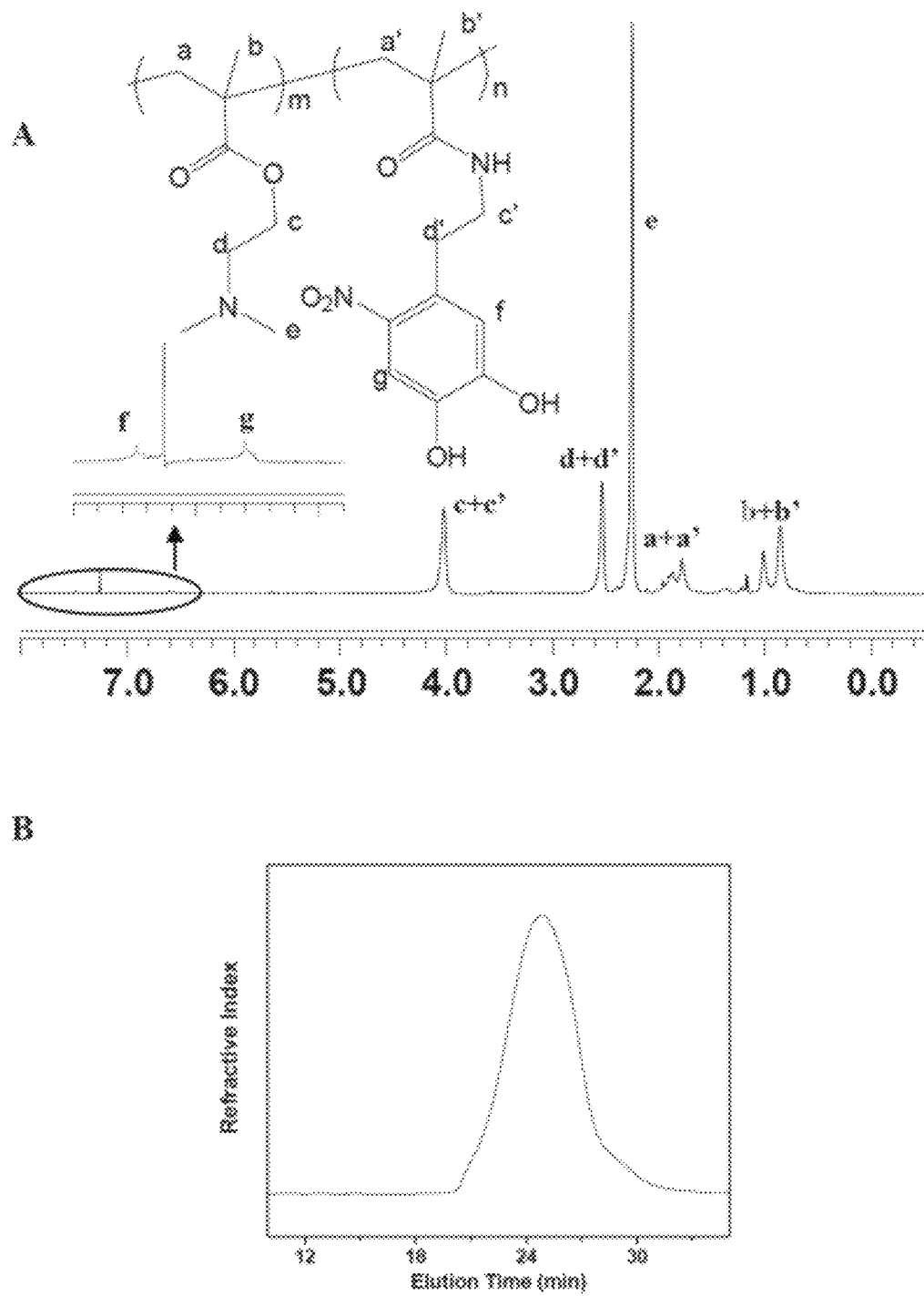
FIG. 17. (A) $^1$H NMR spectrum of PDMA-co-PNDHPMA (3.0 mol % nitro-catechol) copolymer in $CDCl_3$. (B) Aqueous GPC trace of PDMA-co-PNDHPMA copolymer (3 mol % nitro-catechol) at pH 3.5.

Here, the copolymerization was performed in DMF at 60° C. for 24 h and AIBN (2 wt % of two monomers) was used as radical source. Statistical copolymers with nitro-catechol molar ratio of 3 mol % and 15 mol % were synthesized respectively. The molar ratio of nitro-catechol was calculated by $^1$H NMR study based on comparing typical peak e (δ=2.26 ppm) from DMA and peak f and g (δ=6.6 ppm and 7.45 ppm) from nitro-catechol (FIG. 17(A)). The molecular weights of copolymers were obtained from aqueous GPC at pH 3.5 and mono-dispersed PEG was used as standards. Based on calculation of light scattering signal, $M_n$ and PDI for copolymers are 6,800 g/mol, and 2.9 for copolymer with 3 mol % of nitro-catechol (FIG. 17(B), and 7,600 g/mol, and 2.2 for copolymer with 15 mol % of nitro-catechol.

Figure 18:
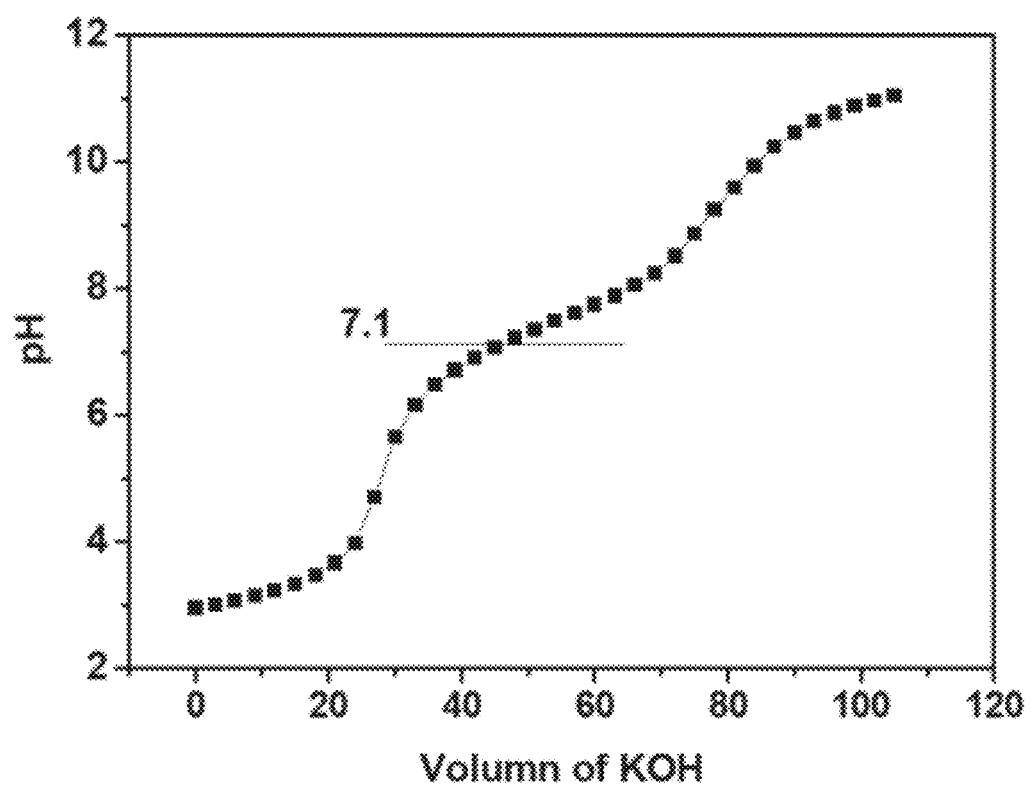
FIG. 18. Titration curve of PDMA-co-PNDHPMA (3 mol % nitro-catechol) copolymer with polymer concentration of 5 mM.

Comparing with catechol, which has a pKa of 9.3, the nitro-substituted catechol has a much lower pKa of 6.7, due to the substitution of electro-withdrawing group. The statistical nitro-catechol containing copolymer would be expected to have a lower pKa. From the titration of copolymer with 3 mol % of nitro-catechol in water, the overall pKa obtained is 7.1 (FIG. 18).

Figure 19:
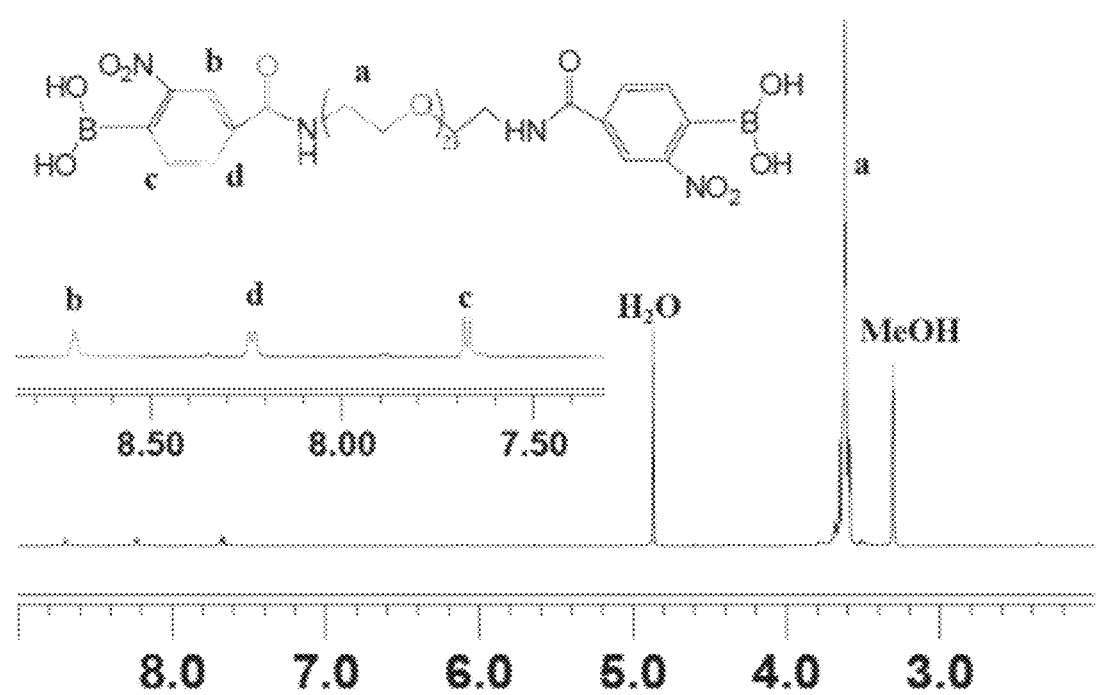
FIG. 19. $^1$H NMR spectrum of NPBA-PEG-NPBA with concentration of 7.5 wt % in MeOD.
Figure 20:
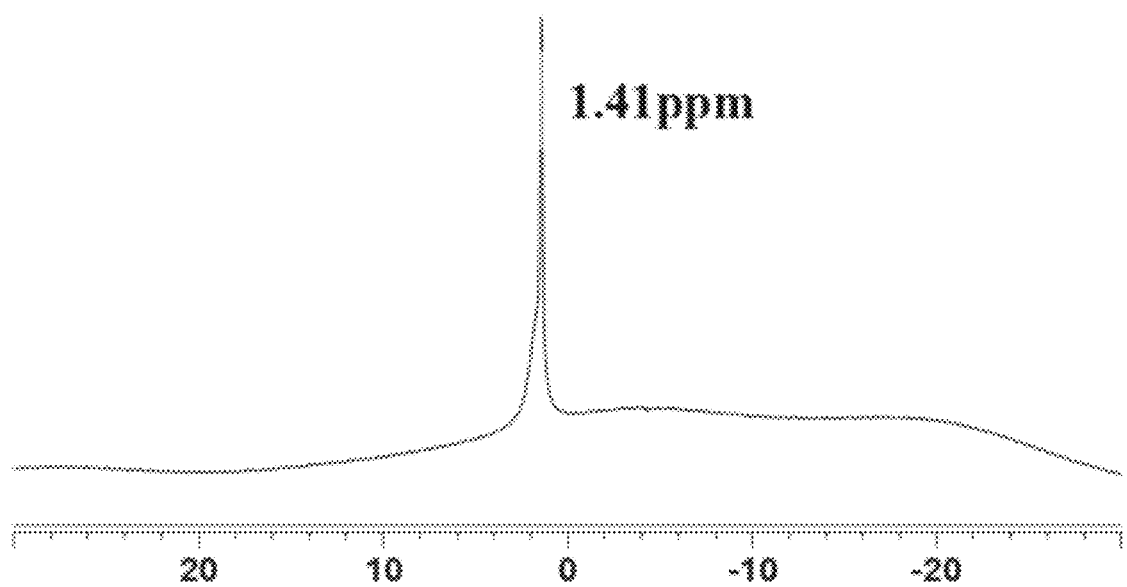
FIG. 20. $^{11}$B NMR spectrum of NPBA-PEG-NPBA in $D_2O$/NaOD with concentration of 7.5 wt %.
Figure 21:
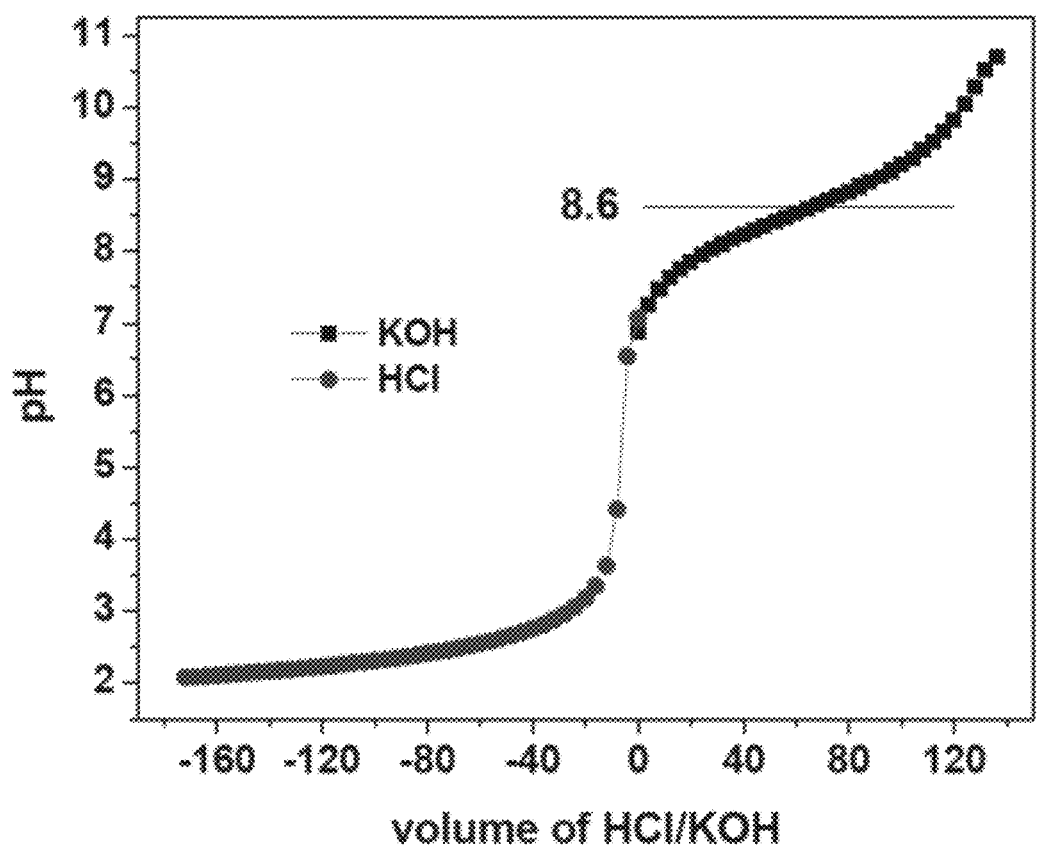
FIG. 21. Titration curve of NPBA-PEG-NPBA obtained in KCl aqueous solution using HCl and KOH. Concentration of NPBA-PEG-NPBA was 5 mM.

Unlike the previously used cross-linker, 1,3-benzenediboronic acid, which has limited solubility at neutral and acidic water, the PEG based cross-linker, NPBA-PEG-NPBA, which was synthesized by coupling reaction of carboxyl group from NPBA with difunctional PEG amine ($NH_2$-PEG-$NH_2$), has good water solubility at any pH range. The functionalized PEG based cross-linker was characterized by $^1H$ NMR study by typical peaks b, c, and d with at chemical shift of 8.70 ppm, 7.67 ppm and 8.37 ppm (FIG. 19) and $^{11}B$ NMR spectrum (FIG. 20). More importantly, from the titration study, the NPBA-PEG-NPBA has a lower pKa of 8.4 (FIG. 21).

After getting both copolymer and cross-linker in hand, we started to make hydrogel. By mixing copolymer solution, which was prepared by dissolving copolymer in PBS buffer with certain concentration, with NPBA-PEG-NPBA solution in PBS buffer at 20° C. at given molar ratio of nitro-catechol to cross-linker, yellow and transparent hydrogel was formed instantly after the mixture solution was vortexed. Here, for copolymer PDMA-co-PNDHPMA (3 mol % nitro-catechol), polymer solution with concentration ranging from 7.5 wt % to 15 wt % were investigated while for copolymer PDMA-co-PNDHPMA with 15 mol % of nitro-catechol, concentration of 7.5 wt % was used only considering the solubility.

Figure 22:
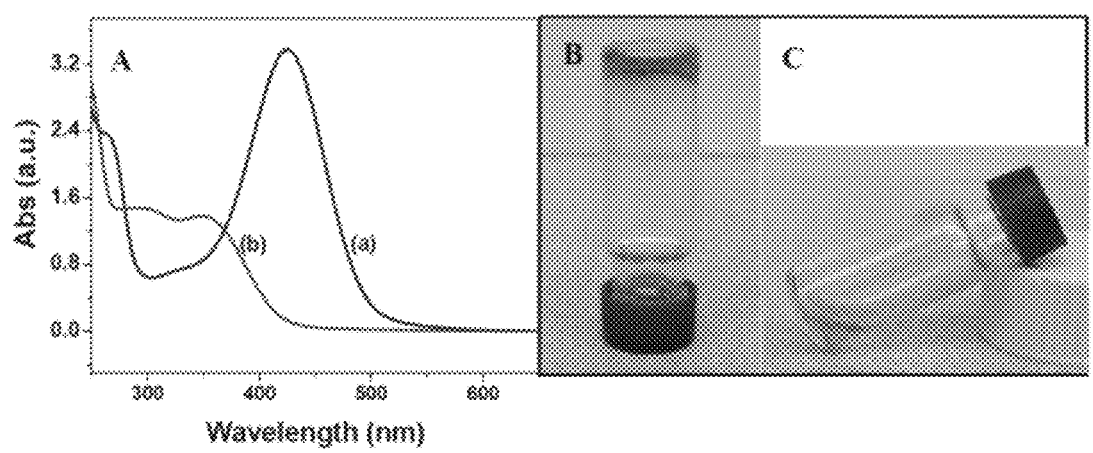
FIG. 22. (A) Uv-vis spectroscopy of mPEG-Ncat/NPBA-PEG-NPBA with 2:1 molar ratio at (a) pH 7.4 and (b) pH 3.0; photographs of hydrogel formed at pH 7.4 (B) and corresponding solution after pH was changed to 3.0 (C) by using PDMA-co-PNDHPMA (3.0 mol % nitro-catechol) copolymer at polymer concentration of 15 wt % at 1:2 molar ratio of nitro-catechol to cross-linker.
Figure 23:
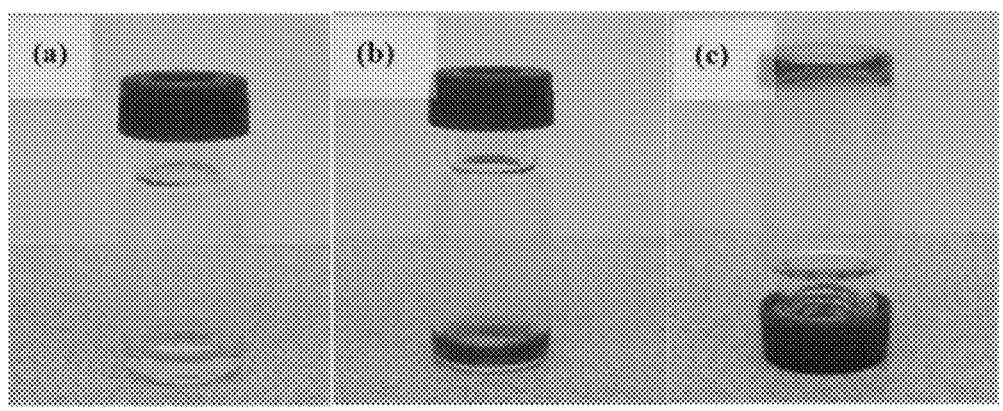
FIG. 23. Photos of (a) PBS buffer solution (pH 7.4) of NPBA-PEG-NPBA, (b) PBS buffer solution of PDMA-co-PNDHPMA (3.0 mol % nitro-catechol) solution and (c) free-standing hydrogels after mixing right amount of solution (a) and (b). Polymer concentration was 15 wt %.

The complexation of nitro-catechol with difunctional cross-linker was studied by using monofunctional nitro-catechol containing polymer, mPEG-Ncat ($M_w$~5000 g/mol). As shown in FIG. 22A, after complexation at pH 7.4 in PBS buffer at a diluted polymer concentration (1.7 wt %) and with a molar ratio of mPEG-Ncat to cross-linker of 2:1, UV-absorption peak at 490 nm attributed to the formation of tetrahedral structure from nitro-catechol-NPBA complexation was generated. In the meantime, the hydrogel is formed which is free-standing as shown in FIG. 22B after mixing copolymer solution with 3 mol % catechol and 15 wt % polymer concentration with NPBA-PEG-NPBA at molar ratio of nitro-catechol to cross-linker of 1:2 (FIG. 23).

Here, the inversion test was adopted for judging the formation of hydrogels. However, after pH was changed to 3 by addition of HCl, the free-standing hydrogels turned into clear flowable solution instantly without any insoluble residues accompanied with the disappearance of peak at 490 nm, indicating a good pH responsiveness of hydrogels (FIG. 22C). Comparing with catechol, nitro-substituted catechol is more stable for the electro withdrawing group of nitro group in the aromatic ring. There is no distinct absorption peak from the partial oxidation of nitro-catechol; showing that nitro-catechol is stable at pH 7.4, which is higher than its pKa.

Figure 24:
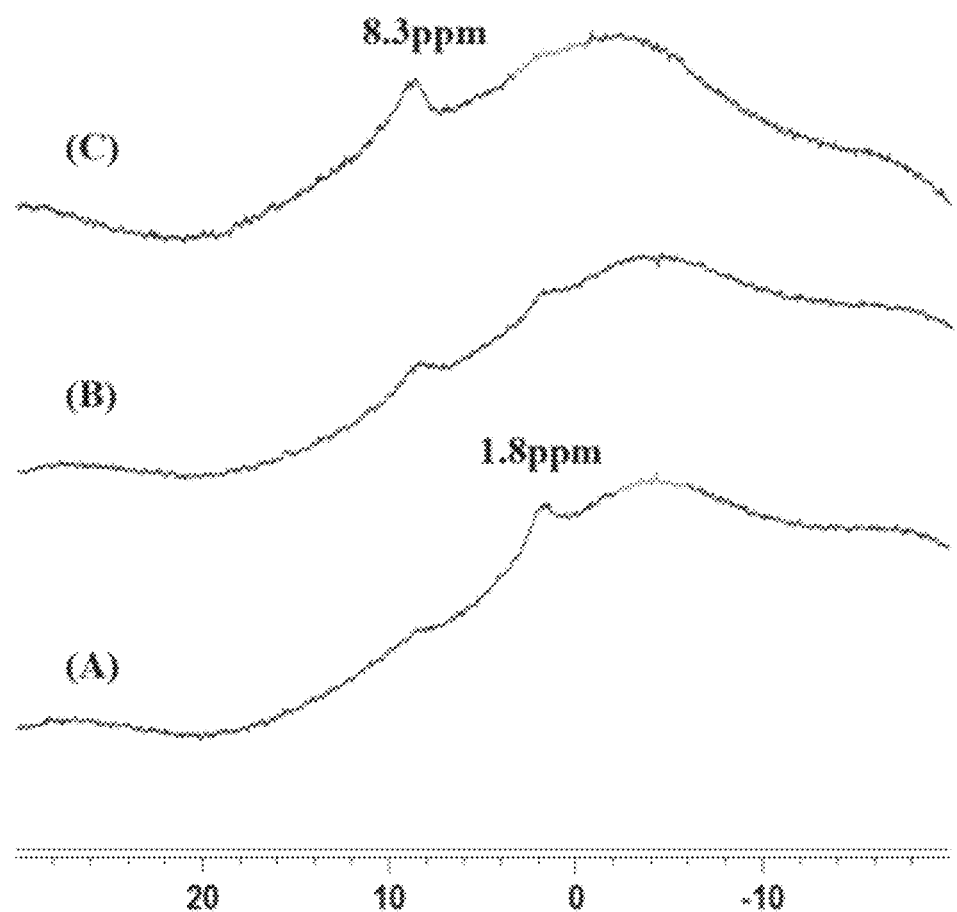
FIG. 24. $^{11}$B NMR spectra of mPEG-Ncat/NPBA-PEG-NPBA at pH≅7.4 in NaOD/$D_2O$ after (A) 30 min, (B) 24 h and (C) 48 h. Polymer concentration was 15 wt % and molar ratio of nitro-catechol to NPBA-PEG-NPBA was 2:1.
Figure 25:
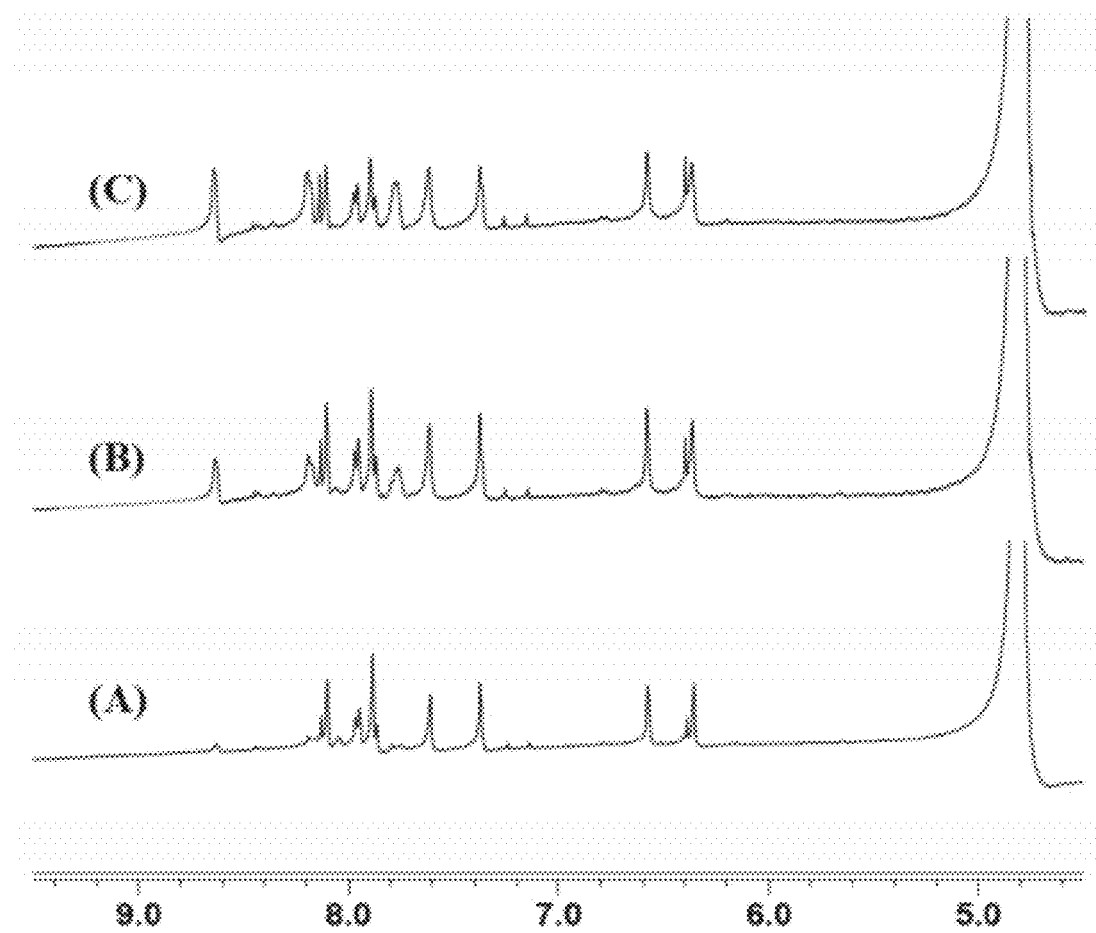
FIG. 25. $^1$H NMR spectra of mPEG-Ncat/NPBA-PEG-NPBA at pH≅7.4 in NaOD/$D_2O$ after (A) 30 min, (B) 24 h and (C) 48 h.

The complexation between nitro-catechol and NPBA was confirmed by $^{11}B$ NMR studies. In order to avoid any cross-linking of polymer with cross-linker, monofunctional nitro-catechol containing polymer, mPEG-Ncat was used as a model molecule to complex with NPBA-PEG-NPBA in $D_2O$/NaOD or $D_2O$/DCl with polymer concentration of 15 wt %. It turned out that at pH of 7-8, a new peak with chemical shift of 8.3 ppm was generated, which is assigned to the tetrahedral structure and consistent with Example 1 showing 4-arm PEG catechol/boronate complexation (FIG. 24). The hydrogels exhibit the ability to stretch into long thread-like dimensions, attributed to the entanglement of these polymers and also to the dynamic cross-linking process. $^1H$ NMR also show that after complexation, new peaks with chemical shift of 6.4 ppm and 7.4 ppm occur, which are assigned to phenyl group protons after complexation. Peaks with chemical shifts of 7.8 ppm, 8.4 ppm and 8.65 ppm were generated as well and increased with the reaction time, indicating that the more cross-linker NPBA-PEG-NPBA were complexed with nitro-catechol (FIG. 25).

The ideal molar ratio of nitro-catechol to cross-linker is 2:1 providing that the complexation is 100%. For copolymer PDMA-co-PNDHPMA containing 3 mol % of nitro-catechol, a systematic study of gelation was performed with various molar ratio of nitro-catechol to cross-linker at polymer concentration ranging from 7.5 wt % to 15 wt %. As shown in Table 2, hydrogels were formed at molar ratio of 4:1, 2:1, 1:1 and 1:2 except that hydrogels were weak at high ratio which resulted in low cross-linking density. Large excessive use of cross-linker did not give hydrogels formation since there is no sufficient nitro-catechol to complex with cross-linker for constructing three dimensional networks.

TABLE 2

Effect of stoichiometry on hydrogel formation at 15 wt % PDMA-co-PNDHPMA (3.0 mol % nitro-catechol) polymer concentration and at pH 7.4.

| Molar Ratio[a] | Gelation Time[b] | Physical State |
|---|---|---|
| 4:1 | 10.0 min | Yellow and transparent gel, viscous |
| 2:1 | 10.0 min | Yellow and transparent gel, viscous |
| 1:1 | 10.0 min | Yellow and transparent gel, free standing |
| 1:2 | 10.0 min | Yellow and transparent gel, free standing |
| 1:3 | — | No gel after 12 hours |
| 1:4 | — | No gel after 12 hours |

[a]nitro-catechol:NPBA-PEG-NBPA;
[b]vial inversion method.

Figure 26:
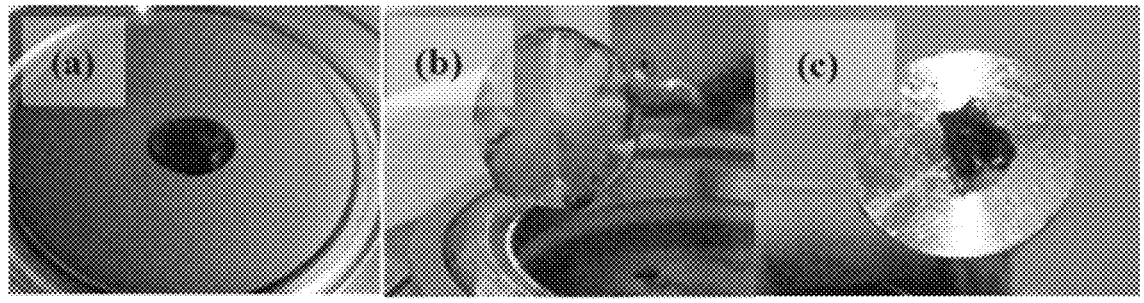
FIG. 26. Hydrogels formed from NPBA-PEG-NPBA and PDMA-co-PNDHPMA (3 mol % nitro-catechol) with polymer concentration of 15 wt %. (a) Aqueous polymer solution in PBS buffer at 15 wt %, (b) hydrogels after angular frequency measurements, and (c) free-standing hydrogel of (b) after scratched together.
Figure 27:
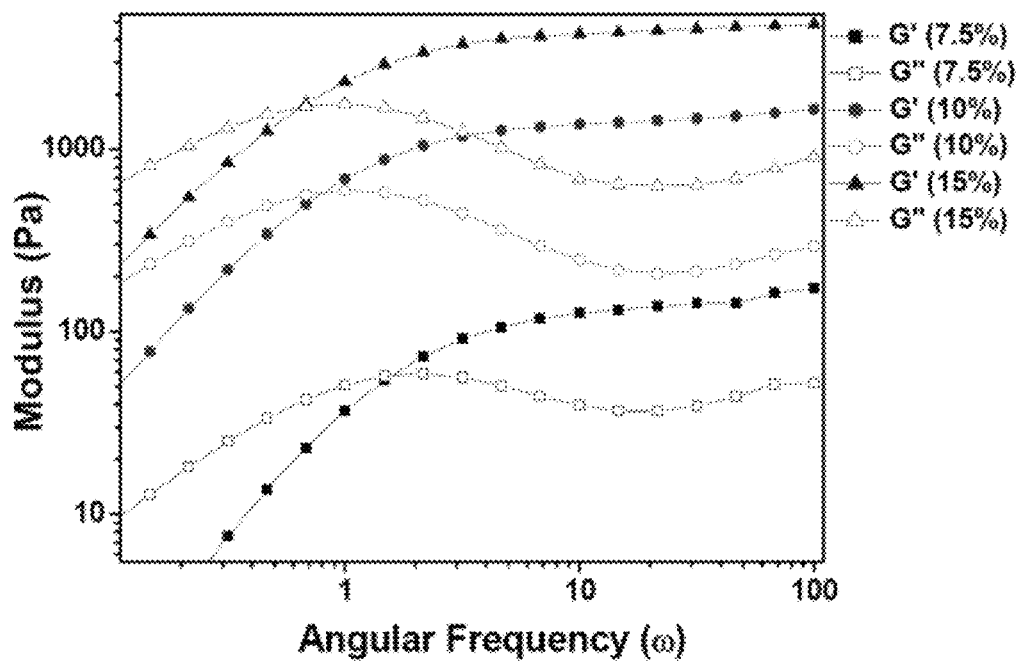
FIG. 27. Dynamic frequency sweep of hydrogels formed from PDMA-co-PNDHPMA/NPBA-PEG-NPBA (3.0 mol % nitro-catechol) with polymer concentration of (a) 15 wt % (b) 10 wt % and (c) 7.5 wt %. The molar ratio of nitro-catechol to NPBA-PEG-NPBA was 1:2 for each polymer concentration.

Gelation behavior was studied by subjecting the hydrogels to dynamic rheology as a function of angular frequency. Typically, hydrogels formed with temporary, reversible bonds are known to display frequency-dependent moduli. The rheological behavior of hydrogels based on complexation of nitro-catechol with NPBA are consistent with the time dependent viscoelastic properties of dynamic hydrogels networks. For hydrogels formed with copolymer containing 3 mol % nitro-catechol, polymer concentration of 7.5 wt %, 10 wt %, and 15 wt % were used, and free-standing hydrogels were formed a few minutes later after rheology measurement (FIG. 26). As shown in FIG. 27, for hydrogels with these three polymer concentrations, G" dominates G' at low angular frequencies while G' dominates G" at high angular frequencies while there is a cross over at approximately 1.0 rads$^{-1}$, indicating that there is no enough time for the labile cross-linking to dissociate, displaying the elastic-like behavior.

The rheology properties of cross-linked hydrogels were further studied by varying polymer concentration. Increasing the polymer concentration resulted in higher moduli, due to a concentration does not alter the reversible nature of the gels but the cross-linking density is changed. In the meantime, the angular frequency at which G' and G" cross over, increased as well with decrease of polymer concentration, indicating a fluid-like liquid are formed with lower polymer concentration due to lower cross-linking density.

Figure 28:
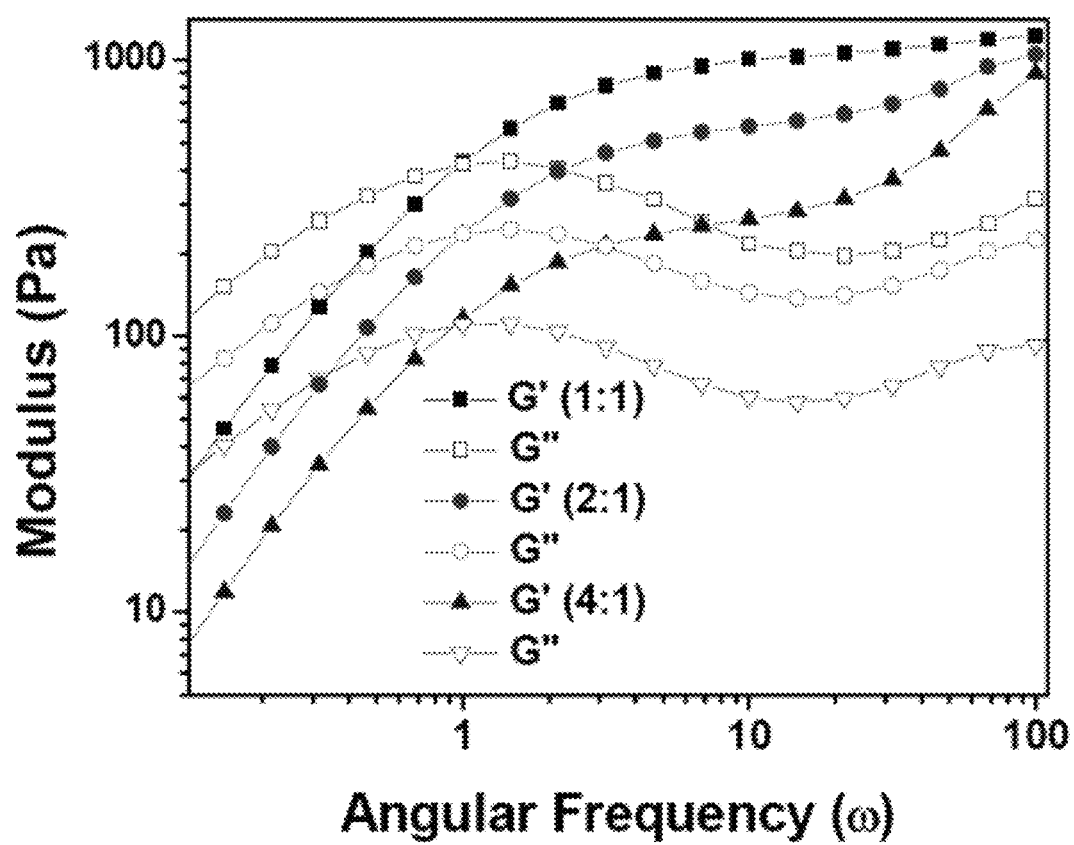
FIG. 28. Dynamic frequency sweep of hydrogels formed from PDMA-co-PNDHPMA/NPBA-PEG-NPBA (3.0 mol % nitro-catechol) at molar ratio of nitro-catechol to cross-linker of (a) 1:1, (b) 2:1 and (c) 4:1. Polymer concentration for each polymer solution was 15 wt %.

The mechanical properties were further studied by varying the molar ratio of nitro-catechol to cross-linker. As shown in FIG. 28, a polymer concentration of 15 wt % was used with varied molar ratio of nitro-catechol to cross-linker at 1:1, 2:1, and 4:1. It is obvious that there is not enough cross-linker at molar ratio of 4:1, while there is excessive cross-linker at ratio of 1:1, and 1:2.

Figure 29:
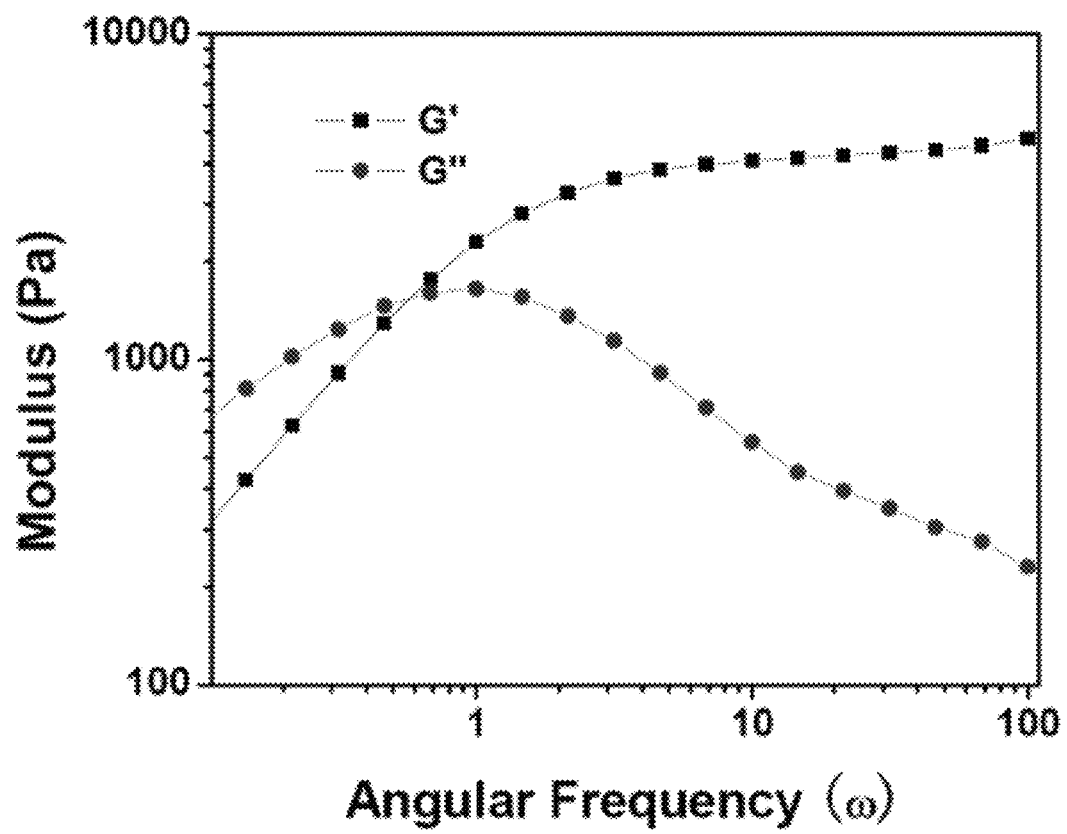
FIG. 29. Dynamic frequency sweep of hydrogels formed from NPBA-PEG-NPBA and PDMA-co-PNDHPMA (15 mol % nitro-catechol) at polymer concentration of 7.5 wt %. The molar ratio of nitro-catechol to cross-linker was 1:1.

For hydrogels formed from polymer containing 15 mol % of nitro-catechol, the moduli (G', G") at polymer concentration of 15 wt % were significantly improved compared with those formed from polymer containing 3 mol % nitro-catechol (FIG. 29) under the same polymer concentration and same molar ratio of nitro-catechol to cross-linker. Both G' and G" were increased about ten times at polymer concentration of 7.5 wt % with 1:2 molar ratio of nitro-catechol to cross-linker. The cross over of G' and G" was decreased as well, indicating a more rigid gel was formed with polymer containing high catechol content.

Figure 30:
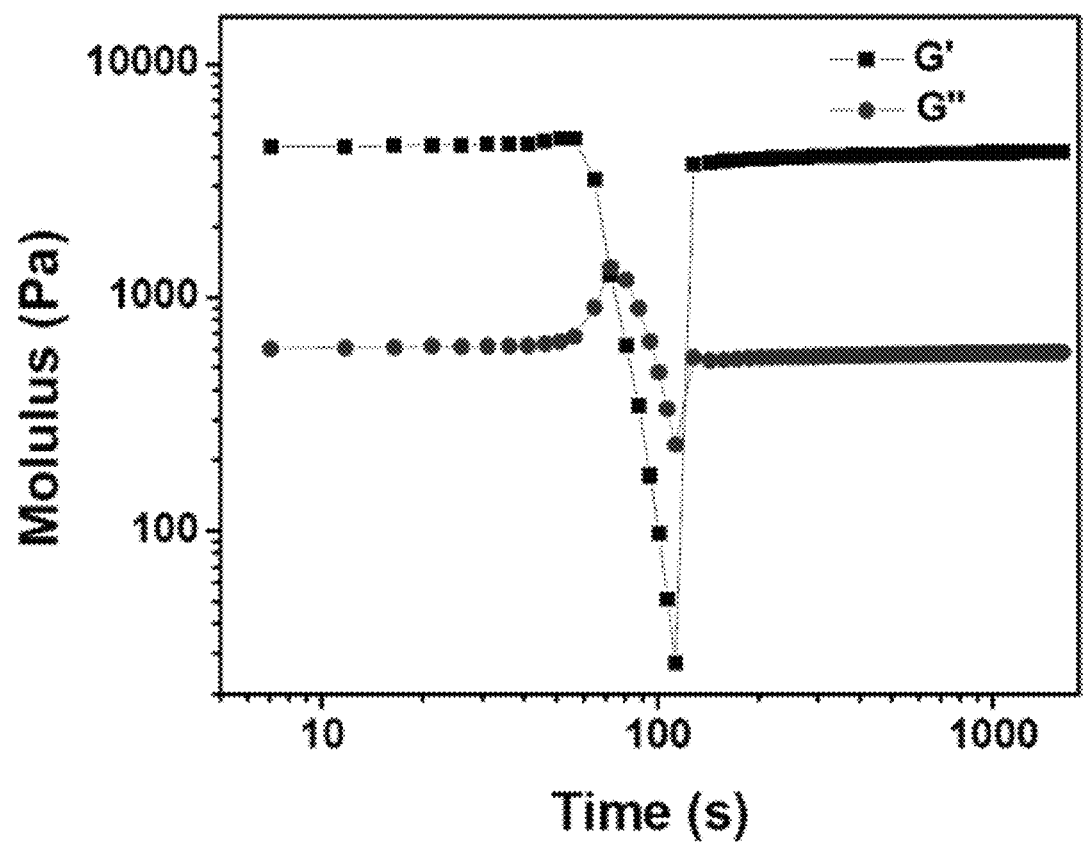
FIG. 30. Time test of hydrogels at 5% strain after hydrogels were destroyed at 1000% strain. 7.5 wt % of polymer (15 mol % nitro-catechol) concentration was used and molar ratio nitro-catechol to cross-linker was 1:2; 93% modulus was recovered one minute after failure and 95% modulus recovered in 25 min.

Similar to Example 1, if these hydrogels have reversible behavior at the molecular scale, they recover to the point of exhibiting the original mechanical properties after being stressed to the point of gel failure. The rheology study of hydrogels with 7.5 wt % PDMA-co-PNDHPMA, which contain 15 mol % of nitro-catechol, confirms this result, as shown in FIG. 30. After loaded with approximately 1000% strain, hydrogels were destroyed while the mechanical property was recovered instantly after the stain was removed, obtaining moduli which are almost the same as before, indicating that complexation of nitro-catechol with NPBA is reversible. The nature of this dynamic reversible complexation mainly contributes to the self-healing property which is achievable for hydrogels with 7.5-15 wt % polymer concentration and under a series of molar ratio of nitro-catechol to cross-linker.

Figure 31:
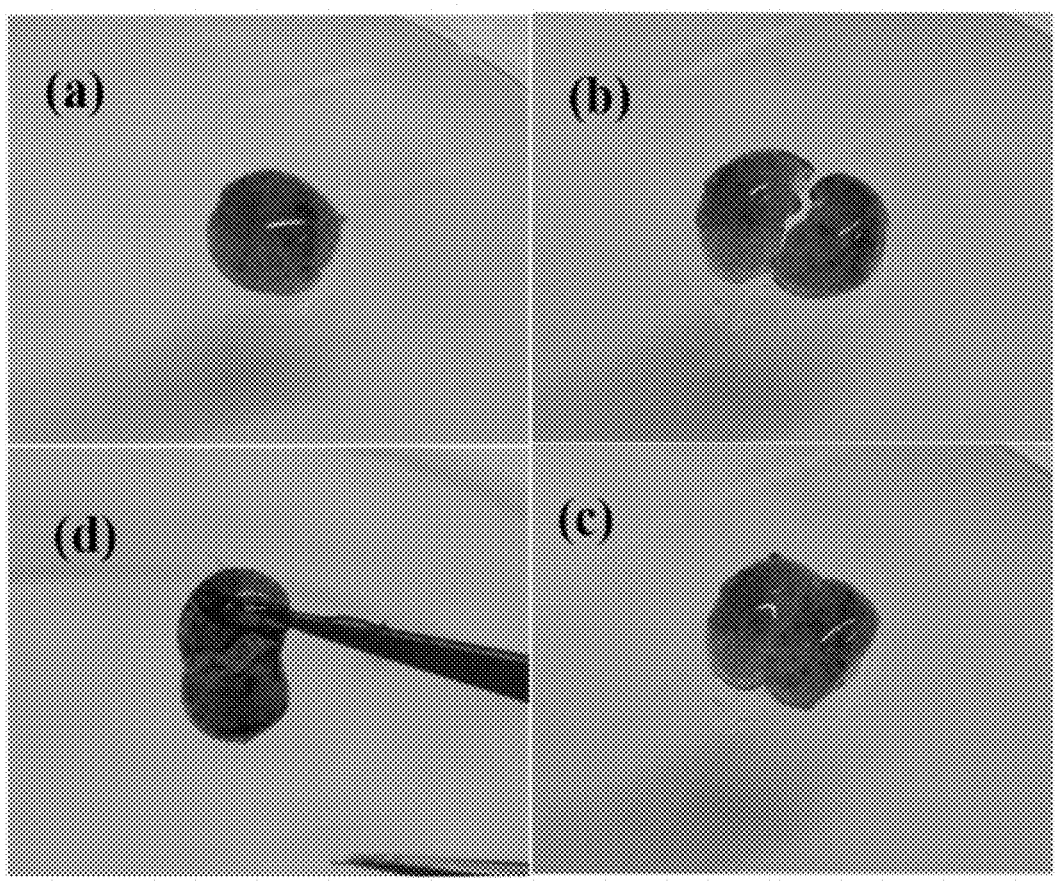
FIG. 31. Self-healing properties of the covalent polymer hydrogel formed from PDMA-co-PNDHPMA (15 wt %, 3 mol % nitro-catechol) and NPBA-PEG-NPBA at pH 7.4. The gel was formed on polystyrene substrate (a), stretch gel with a tweezer (b), put it back (c), and fused together. The molar ratio of nitro-catechol to NPBA-PEG-NPBA was 1:2. Hydrogel is sticky to touch and adhesive.
Figure 32:
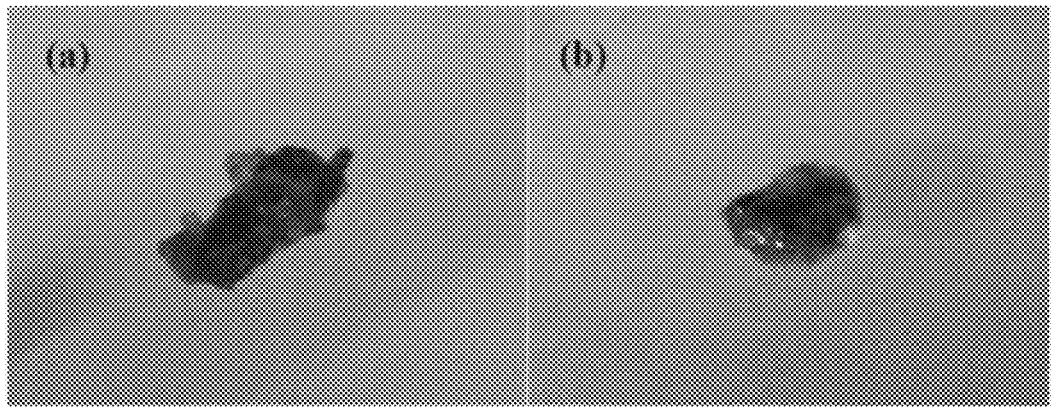
FIG. 32. Self-healing properties of the covalent polymer hydrogels formed from PDMA-co-PNDHPMA (15 mol % catechol, 7.5 wt %) and NPBA-PEG-NPBA at pH 7.4 with 1:2 molar ratio of nitro-catechol to cross-linker. (a) hydrogel formed after 10 min and (b) after 12 hours.
Figure 33:
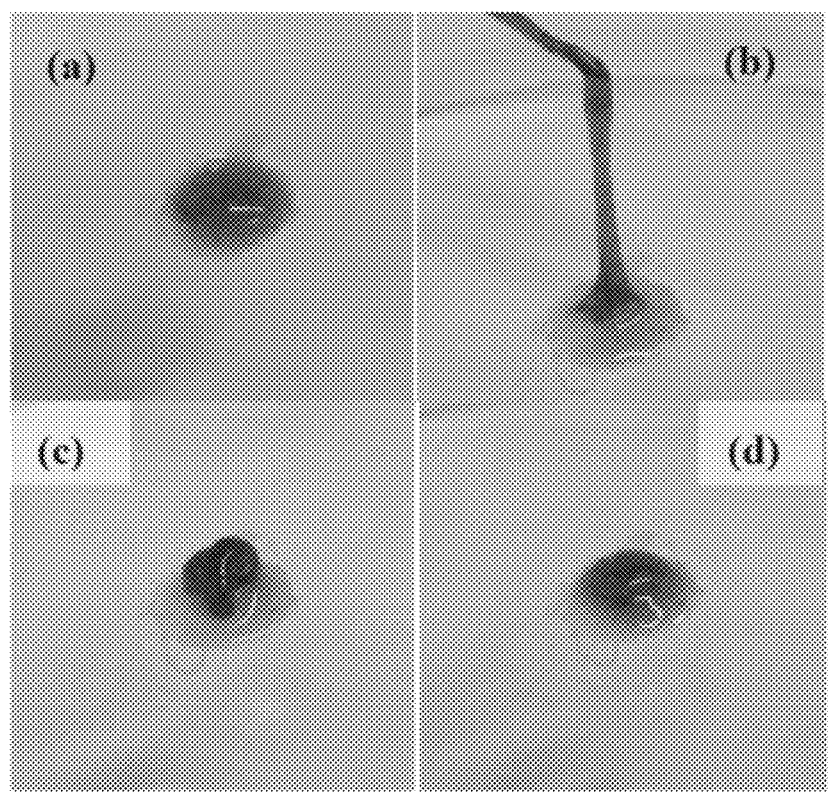
FIG. 33. Self-healing properties of the covalent polymer gel formed from PDMA-co-PNDHPMA (15 wt %) and NPBA-PEG-NPBA at pH 7.4. The hydrogel was formed on polystyrene substrate (a), stretch gel with a tweezers (b), put it back (c), and fused together. 15 wt %, nitro-catechol: cross-linker was 4:1, gel is adhesive.

As shown in FIG. 31, after cutting hydrogels into two pieces (FIG. 31a), and put them together (FIG. 31b), they merged to form a whole piece in 30 seconds for hydrogels which were prepared with 15 wt % of PDMA-co-PNDHPMA (3.0 mol % nitro-catechol) polymer at 1:2 molar ratio of nitro-catechol to NPBA-PEG-NPBA. The merged hydrogels were able to be vertically picked up with tweezer without breaking (FIG. 31d). If this hydrogels are messed up, it recovers to form a smooth surface in hours depending on the polymer concentration. For hydrogels formed with 7.5 wt % of PDMA-co-PNDHPMA (15 mol % nitro-catechol) and cross-linked with 1:2 molar ratio of nitro-catechol to NPBA-PEG-NPBA, hydrogels recover in couple of hours from a totally messed up shape to a gel with smooth surface (FIG. 32). For hydrogels formed with a molar ratio of 4:1, it is stretchable and self-heals as well (FIG. 33). From our previous and current study, $^{11}$B NMR showed that complexation was not 100% even after 48 h. As with other reversible reactions, the unreacted nitro-catechol will diffuse into the new interface and complex with NPBA, resulting in the reformation of covalent bonds and new crosslinked hydrogels.

Figure 34:
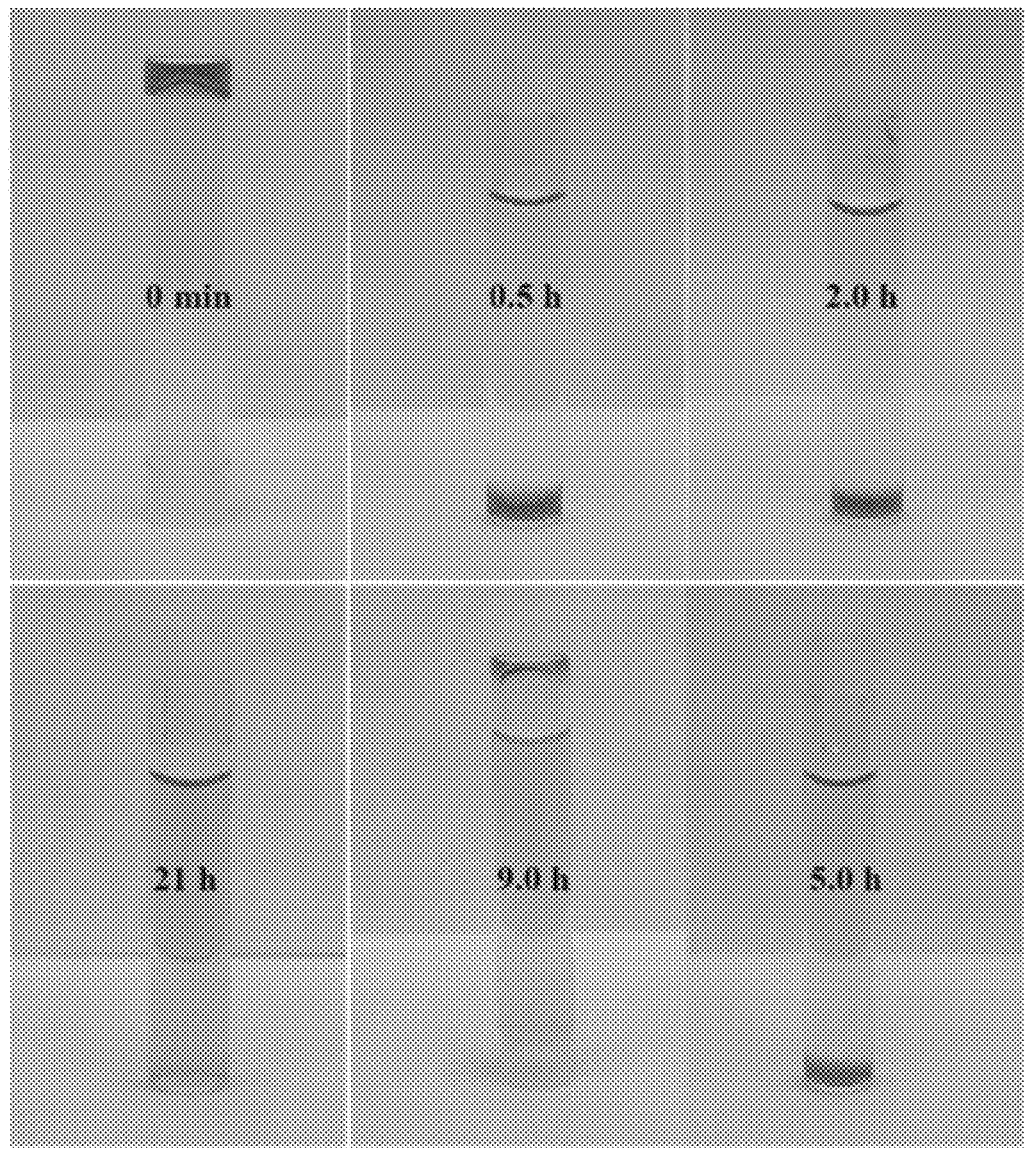
FIG. 34. Hydrogels disassociation study in PBS buffer (pH 7.4) at 37° C. Polymer containing 3 mol % of nitro-catechol was used at concentration of 15 wt % and 1:1 molar ratio of nitro-catechol to NPBA-PEG-NPBA.
Figure 35:
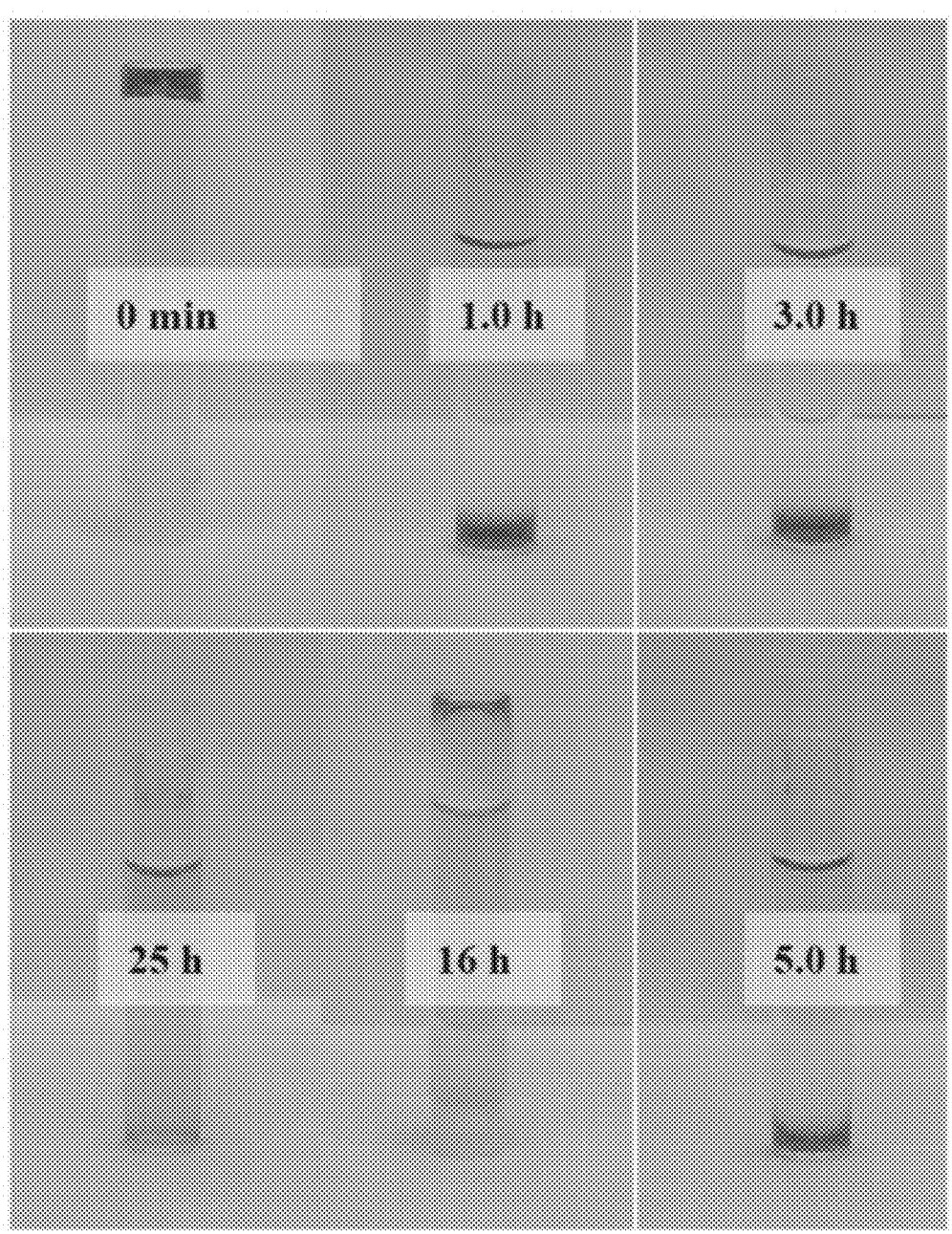
FIG. 35. Stability studies of hydrogels in PBS buffer at 20° C. Experimental conditions: 1.0 mL of PBS buffer was added into 0.1 ml hydrogel which was crosslinked with 1:1 molar ratio of nitro-catechol to cross-linker at polymer (3 mol % nitro-catechol) concentration of 15 wt %.

The stability of hydrogels in PBS buffer at 20° C. and 37° C. were studied considering the potential controlled drug release application. Polymer hydrogels which are free-standing with polymer concentration of 15 wt % were used for both temperatures and ten fold of PBS buffer was used for each case. At 37° C., hydrogels disassociated gradually and the released polymers were dissolved in buffer, giving a clear yellow solution on top of hydrogels. About one third of hydrogels were dissolved in 9 h while hydrogels were totally dissolved in 21 hours, resulting in a clear polymer aqueous solution without any insoluble residues (FIG. 34). The disassociation at 20° C. is quite similar to that at 37° C. and hydrogels were dissolved in 25 hours (FIG. 35). The gradual disassociation of nitro-catechol-NPBA in this hydrogel afforded hydrogel a big step for in vivo drug delivery study at physiological pH conditions.

The gelation based on nitro-catechol containing polymer with NPBA-PEG-NPBA cross-linker is a generic method, as confirmed by using statistical copolymers, P(OEGMA)-co-P(NDHPMA) (10 mol % of nitro-catechol). After mixing polymer with 15 wt % concentration with cross-linker NPBA-PEG-NPBA at ratio of nitro-catechol to cross-linker of 1:2 in PBS buffer, free standing hydrogel was formed at physiological pH conditions. By carefully choosing the monomers used, it is feasible to make hydrogels with special properties. In the meantime, a cross-linker, 4-phenylboronic acid PEG 4-phenylboronic acid (PBA-PEG-PBA) without nitro-substitution was synthesized to study the complexation at physiological pH condition with POEGMA-co-PNDHPMA copolymer. The results showed that in our system, polymers containing nitro-catechol groups are able to complex with both NPBA-PEG-NPBA and BPA-PEG-PBA at physiological pH condition, because these two cross-linker have similar pKa (see Table 3).

TABLE 3

Summary of the pKa for both cross-linkers and statistical copolymers.

| Cross-liner/copolymer | Pka |
| --- | --- |
| NPBA-PEG-NPBA | 8.4 |
| NPA-PEG-NPA | 8.8 |
| P(DMA)-co-P(NDHPMA) | 7.1 |
| P(OEGMA)-co-P(NDHPMA) | 6.7[23] |

In conclusion, novel pH responsive and self-healing hydrogels based on complexation of nitro-catechol with NPBA at physiological pH condition were synthesized after the pKa of catechol was lowered by introducing electron-withdrawing group. The moduli of hydrogels are dependent on copolymer composition, copolymer concentration and the molar ratio of nitro-catechol to NPBA. The hydrogels are stable at pH 7.4 while disassociated instantly at acidic condition like pH 3 at 20° C. and can dissolve gradually in PBS buffer (pH 7.4) at both 37° C. and 20° C. in 24 hours, indicating the potential applications for controlled drug release at physiological conditions. Due to this reversible complexation between nitro-catechol and NPBA, hydrogels possess self-healing property and have potential applications in tissue engineering as wound dressings.

Example 3

Biocompatibility of Hydrogel formed by POEGMA-co-PNDHPMA Complexation

In Example 2 above, we reported the formation of hydrogels formed by POEGMA-co-PNDHPMA complexation. In this example, we report the results of a mammalian cell-viability assessment showing that the hydrogels of the disclosed hydrogels are non-toxic, and thus biocompatible. These results demonstrate that the disclosed hydrogels may be safely used for a variety of in-vivo applications, such as in tissue engineering and drug delivery applications.

Cell viability was measured using a proliferative MTS assay. 3T3 fibroblasts were seeded in a multi-well culture plate, maintained and incubated, and exposed to the hydrogel made from POEGMA-co-PNDHPMA complexation at 37° C. for 24 to 48 h. 2-(4',5'-dimethyl-2'-thiazolyl)-3-(4'-sulfophenyl) (MTS) solution was then added to each well; the MTS in metabolically active cells is converted into a colored, soluble formazan product. Absorbance at 490 nm was recorded with a well plate ELISA reader. Each experiment was repeated three times.

Figure 36:
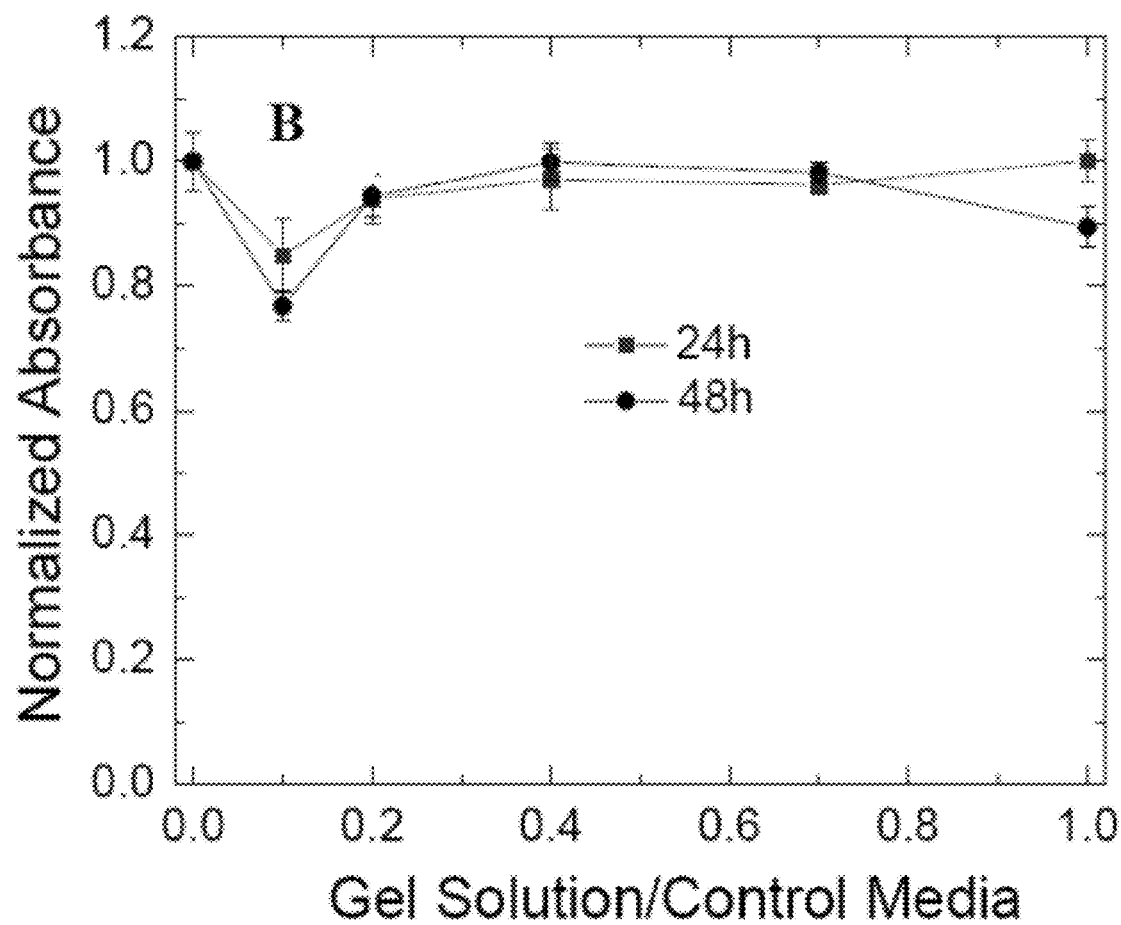
FIG. 36. Mammalian cell viability assessment. MTS assay was used to determine the effect of the gel solution from POEGMA-co-PNDHPMA on 3T3 fibroblasts. At 24 and 48 h time points, cells appear viable at all ratios of POEGMA-co-PNDHPMA gel solution/control media. Error bars represent the standard deviation of 3 samples.

At 24 and 48 h time points, cells appear viable at all ratios of POEGMA-co-PNDHPMA gel solution/control media (see FIG. 36). This data provides further evidence of the viability of using the disclosed hydrogels for in vivo in biomedical applications.

While the present invention has been described in what is perceived to be the most practical and preferred embodiments and examples, it is to be understood that the invention is not intended to be limited to the specific embodiments set forth above. Rather, it is recognized that modifications may be made by one of skill in the art of the invention without departing from the spirit or intent of the invention and, therefore, the invention is to be taken as including all reasonable equivalents to the subject matter of the appended claims.

We claim:

1. A biocompatible pH-responsive self-healing hydrogel comprising a cross-linked polymer comprising:
    (a) a plurality of macromonomers each comprising at least four terminal catechol moieties and having a molecular weight of 1,000 to 20,000 Daltons; and
    (b) one or more cross-linkers each comprising two or more terminal boronic acid moieties;
    wherein the catechol moieties of the macromonomers are covalently bonded to the boronic acid moieties of the cross linker to form a tetrahedral borate ester, wherein the macromonomers are cross-linked into the polymer when the macromonomers are at physiological pH or above and the polymer dissociates into the macromonomers at pH 3.0.

2. The hydrogel of claim 1, wherein the macromonomers have a molecular weight of 5,000 to 15,000 Daltons.

3. The hydrogel of claim 1, wherein the macromonomers are polyethylene glycols or (dihydroxyphenyl)ethyl methacrylamide copolymers.

4. The hydrogel of claim 3, wherein the polyethylene glycols are 4-arm polyethylene glycols wherein each arm is terminated with a catechol moiety.

5. The hydrogel of claim 4, wherein the 4-arm polyethylene glycols have the structure:

6. The hydrogel of claim 3, wherein the (dihydroxyphenyl)ethyl methacrylamide copolymers are comprised of (dihydroxyphenyl)ethyl methacrylamide monomers wherein the phenyl group is nitro substituted.

7. The hydrogel of claim 3, wherein the (dihydroxyphenyl)ethyl methacrylamide copolymers have the structure:

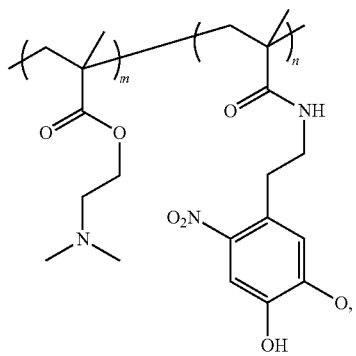

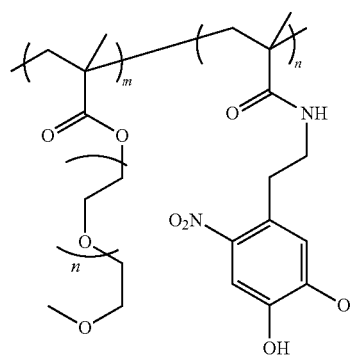

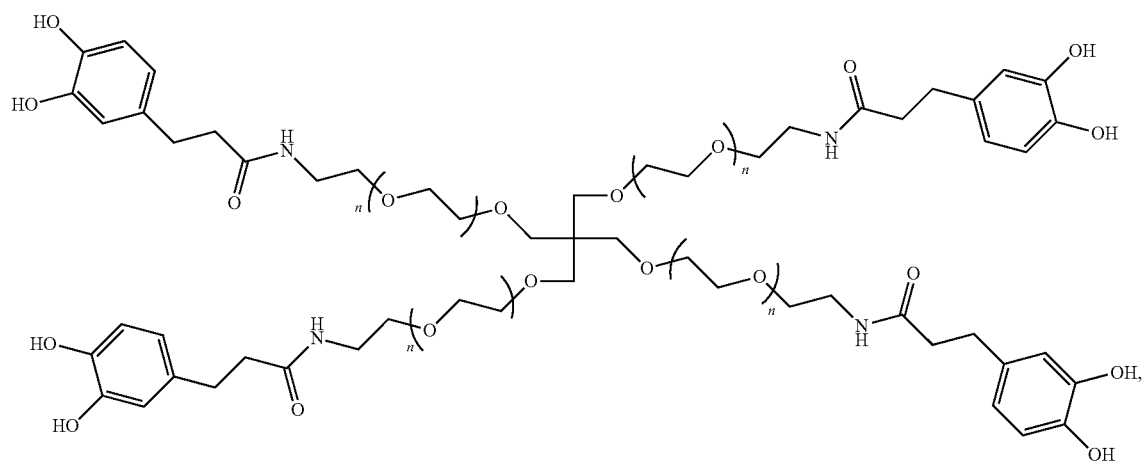

wherein each n is independently selected to be from 1 to 200.

-continued

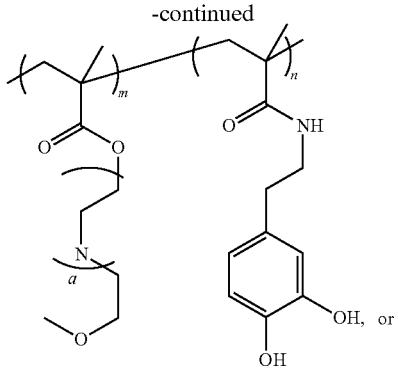

wherein each of m, n and a are independently selected to be from 1 to 200.

8. The hydrogel of claim 1, wherein two terminal boronic acid moieties on the cross-linkers are attached to an aromatic ring.

9. The hydrogel of claim 8, wherein the two terminal boronic acid moieties on the cross linkers are either attached to the same aromatic ring or to two different aromatic rings on opposite ends of the cross-linkers.

10. The hydrogel of claim 8, wherein the cross-linkers have the structure:

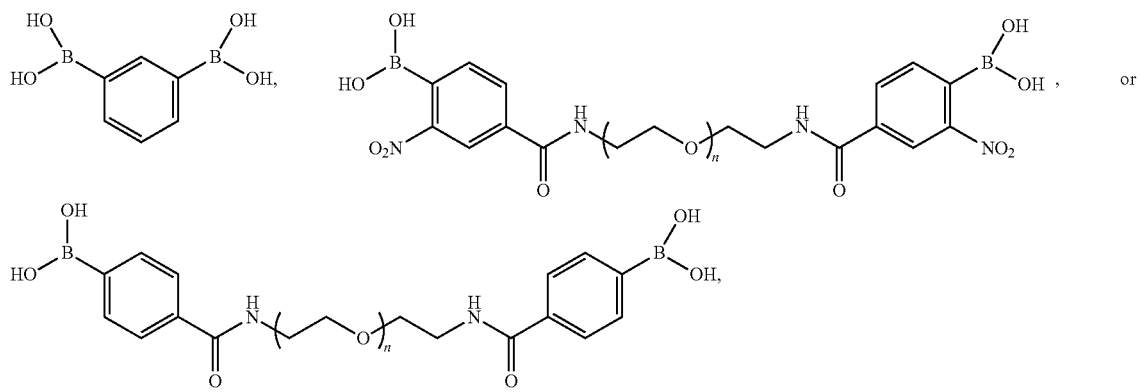

wherein n is from 1 to 100.

11. The hydrogel of claim 1, wherein the tetrahedral borate ester group covalently bonding the macromonomers to the cross-linkers has the structure:

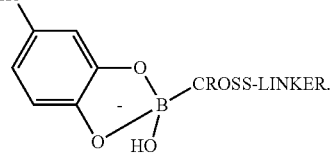

* * * * *

UNITED STATES PATENT AND TRADEMARK OFFICE
CERTIFICATE OF CORRECTION

PATENT NO. : 9,572,910 B2
APPLICATION NO. : 13/476422
DATED : February 21, 2017
INVENTOR(S) : Phillip B Messersmith et al.

Page 1 of 1

It is certified that error appears in the above-identified patent and that said Letters Patent is hereby corrected as shown below:

On the Title Page

Column 1, Line 17 - "grant numbers RC1 DE020702 and R37 DE014193 awarded" should be
-- RC1 DE020402 and R37 DE014193 awarded --

Signed and Sealed this
Tenth Day of October, 2017

Joseph Matal
*Performing the Functions and Duties of the*
*Under Secretary of Commerce for Intellectual Property and*
*Director of the United States Patent and Trademark Office*